(12) United States Patent
Bartlett

(10) Patent No.: US 10,182,926 B2
(45) Date of Patent: Jan. 22, 2019

(54) LIMB PROSTHESIS SYSTEM AND METHOD

(71) Applicant: Brian Bartlett, Seattle, WA (US)

(72) Inventor: Brian Bartlett, Seattle, WA (US)

(*) Notice: Subject to any disclaimer, the term of this patent is extended or adjusted under 35 U.S.C. 154(b) by 498 days.

(21) Appl. No.: 14/470,905

(22) Filed: Aug. 27, 2014

(65) Prior Publication Data

US 2016/0058580 A1 Mar. 3, 2016
US 2017/0209289 A9 Jul. 27, 2017

Related U.S. Application Data

(63) Continuation-in-part of application No. 12/925,997, filed on Nov. 4, 2010, now Pat. No. 9,895,239, which is a continuation-in-part of application No. 11/241,831, filed on Sep. 30, 2005, now Pat. No. 7,828,856.

(60) Provisional application No. 60/614,859, filed on Sep. 30, 2004.

(51) Int. Cl.
*A61F 2/64* (2006.01)
*A61F 2/60* (2006.01)

(52) U.S. Cl.
CPC ............. *A61F 2/642* (2013.01); *A61F 2/604* (2013.01)

(58) Field of Classification Search
CPC ...... A61F 2/60; A61F 2/64; A61F 2/80; A61F 2002/5007; A61F 2/604; A61F 2/642
See application file for complete search history.

(56) References Cited

U.S. PATENT DOCUMENTS

| | | | | | |
|---|---|---|---|---|---|
| 3,922,727 | A * | 12/1975 | Bianco | ...... | A61F 2/76 623/24 |
| 5,387,246 | A * | 2/1995 | Phillips | ...... | A61F 2/602 36/117.1 |
| 6,306,178 | B1 * | 10/2001 | Kania | ...... | A61F 2/60 623/27 |
| 7,288,118 | B1 * | 10/2007 | Swanson, Sr. | ...... | A61F 2/60 623/27 |
| 2005/0059908 | A1 * | 3/2005 | Bogert | ...... | A61F 5/0102 601/5 |
| 2006/0167546 | A1 * | 7/2006 | Bartlett | ...... | A61F 2/60 623/11.11 |
| 2009/0299490 | A1 * | 12/2009 | Summit | ...... | A61F 2/7812 623/27 |
| 2011/0054634 | A1 * | 3/2011 | Bartlett | ...... | A61F 2/60 623/33 |

(Continued)

*Primary Examiner* — Bruce E Snow
*Assistant Examiner* — Melissa Hoban
(74) *Attorney, Agent, or Firm* — Charles J. Rupnick Attorney at Law

(57) ABSTRACT

A prosthesis system can have an advantageous use over conventional prostheses in certain activities, including, but not limited to certain sports activities: The system includes, elastic member(s) that can store and release energy. The storing and releasing of energy in the elastic members happens during the movements made by the user and with the application of the user's own body weight while performing an activity. Implementations can also include a variety of routing configurations for the elastic member(s), as well as a variety of mounting points to integrate the elastic member(s) into the system, and/or a variety of adjustable anti-hyperextension members, and/or a variety of interchangeable shoes used for applicable activities.

19 Claims, 37 Drawing Sheets

(56) References Cited

U.S. PATENT DOCUMENTS

2011/0098828 A1* 4/2011 Balboni .................. A61F 2/60
                                                                                   623/40

* cited by examiner

LIMB PROSTHESIS SYSTEM AND METHOD

This application is a Continuation-in-part of copending parent U.S. patent application Ser. No. 12/925,997 filed in the name of Brian Bartlett on Nov. 4, 2010, which claims priority benefit of copending parent U.S. patent application Ser. No. 11/241,831 filed in the name of Brian Bartlett on Sep. 30, 2005, now allowed, and copending U.S. Provisional Patent Application Ser. No. 61/870,773 filed in the name of Brian Bartlett on Aug. 27, 2013, the complete disclosures of which are incorporated herein by reference.

FIELD OF THE INVENTION

The present invention relates generally to prosthesis systems.

BACKGROUND OF THE INVENTION

Conventional prosthesis systems can be difficult to use for various activities including some involving certain sports.

SUMMARY OF THE INVENTION

The present invention is a prosthesis system for a human limb that allows for energy to be stored and released via one or more elastic member(s) for many activities, including, but not limited to sports activities such as bicycling, surfing, wakeboarding, snowboarding, downhill skiing, cross country skiing, and waterskiing.

According to one aspect of the prosthesis system, the prosthesis system includes a proximate or upper portion configured for coupling with the human limb; a distal or lower portion configured for coupling with an appendage; a joint portion with the proximate or upper portion hingedly coupled to the distal or lower portion via the joint portion such that the distal portion and the proximate portion are pivotally movable with respect to one another between an extended state and a bent state; and an elongated elastic cord member comprising a relatively elastic portion between relatively rigid first and second end portions and substantially continuous therewith, wherein the first end portion is coupled to a first retainer positioned on the proximate or upper portion, and the second end portion is coupled to a second retainer positioned on the distal or lower portion.

A method of making and operating the prosthesis system is detailed herein.

Other aspects of the invention are detailed herein.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF PREFERRED EMBODIMENT

Figure 1:
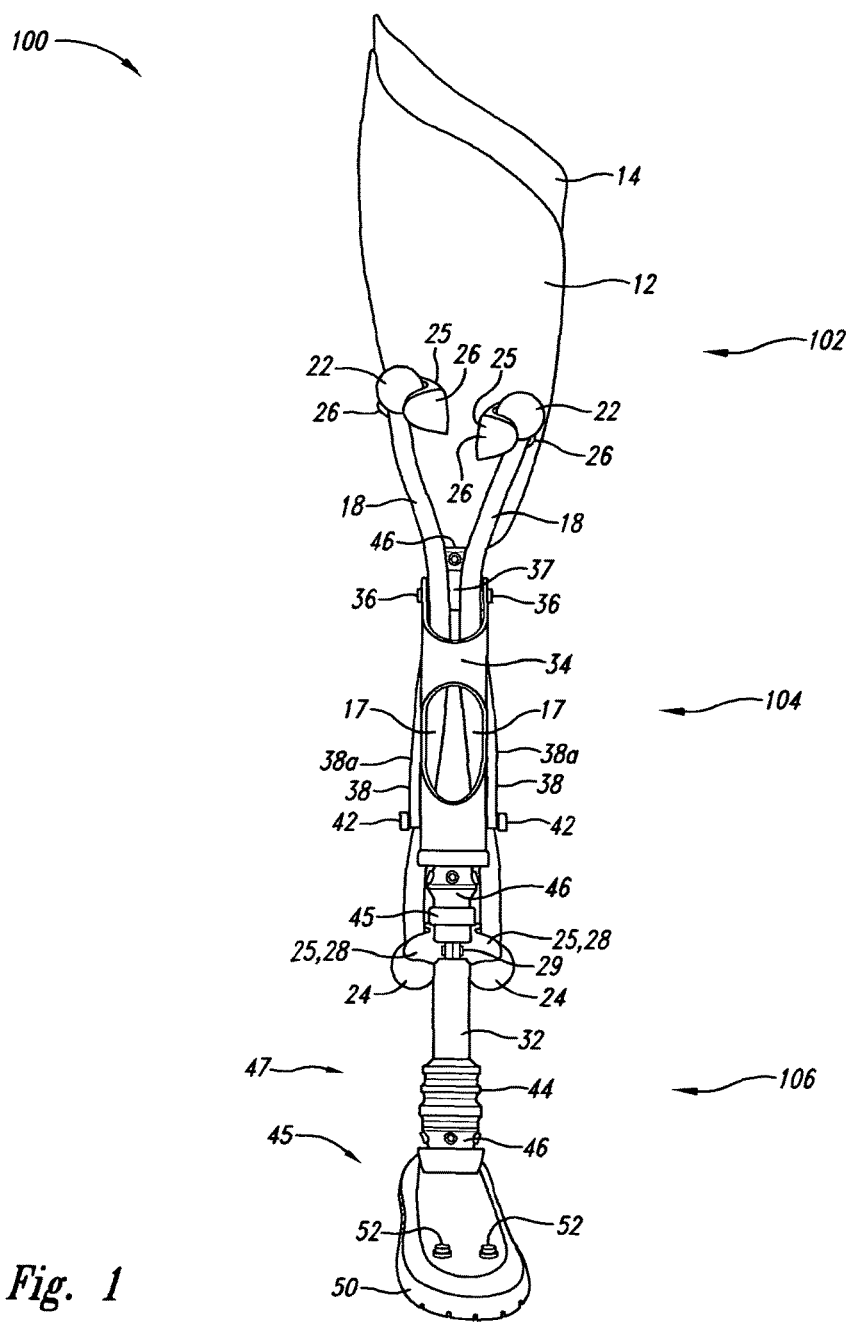
FIG. 1 is a front elevational view of an implementation of a prosthesis system shown in the resting position, having two elastic members routed through the knee frame, and shown with an adjustable strap acting as an anti-hyperextension member.

As required, a detailed illustrative embodiment of the present prosthesis system and method is disclosed herein. However, techniques, systems and operating structures in accordance with the present prosthesis system and method may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein which define the scope of the present prosthesis system and method. The following presents a detailed description of an illustrative embodiment (as well as some alternative embodiments) of the present prosthesis system and method.

In the Figures, like numerals indicate like elements.

A prosthesis system described herein allows for energy to be stored and released via one or more elastic member(s). Based upon this approach potential exists for performance advantages over a conventional prosthesis, such as when used in activities requiring the use muscles such as extensor muscles, for instance, the quadriceps. Present implementations can have an advantageous use over conventional prostheses in many activities, including, but not limited to sports activities such as bicycling, surfing, wakeboarding, snowboarding, downhill skiing, cross country skiing, and waterskiing. The system includes, elastic member(s) that can store and release energy. The storing and releasing of energy in the elastic members happens during the movements made by the user and with the application of the user's own body weight while performing an activity. Implementations can also include a variety routing configurations for the elastic member(s), as well as a variety of mounting points to integrate the elastic member(s) into the system, and/or a variety of adjustable anti-hyperextension members, and/or a variety of interchangeable shoes used for applicable activities.

Represented herein is a prosthesis system 100 comprised of an upper portion 102, a joint portion 104, and a lower portion 106. Further included in the system is one or more elastic member(s) 18 for storing and releasing energy, an adjustable anti-hyperextension member 38 that prevents the elastic members 18 from hyper extending the system, a resilient ankle joint 44 in the ankle segment 47 that allows for three-dimensional movement of a foot or other appendage 48 relative to the lower portion 106, and/or foot 48 in which a shoe 50 may be changed accordingly to accommodate any various activities the user may wish to engage in.

The implementations shown herein are representing a right leg. A left leg would simply be a mirror image of the right leg, and would incorporate all of the same components, forces, and workings of the right leg. Alternately, all of these same components, forces, and/or workings could also be applied to an elbow, a wrist, a shoulder, and/or an ankle.

Figure 6:
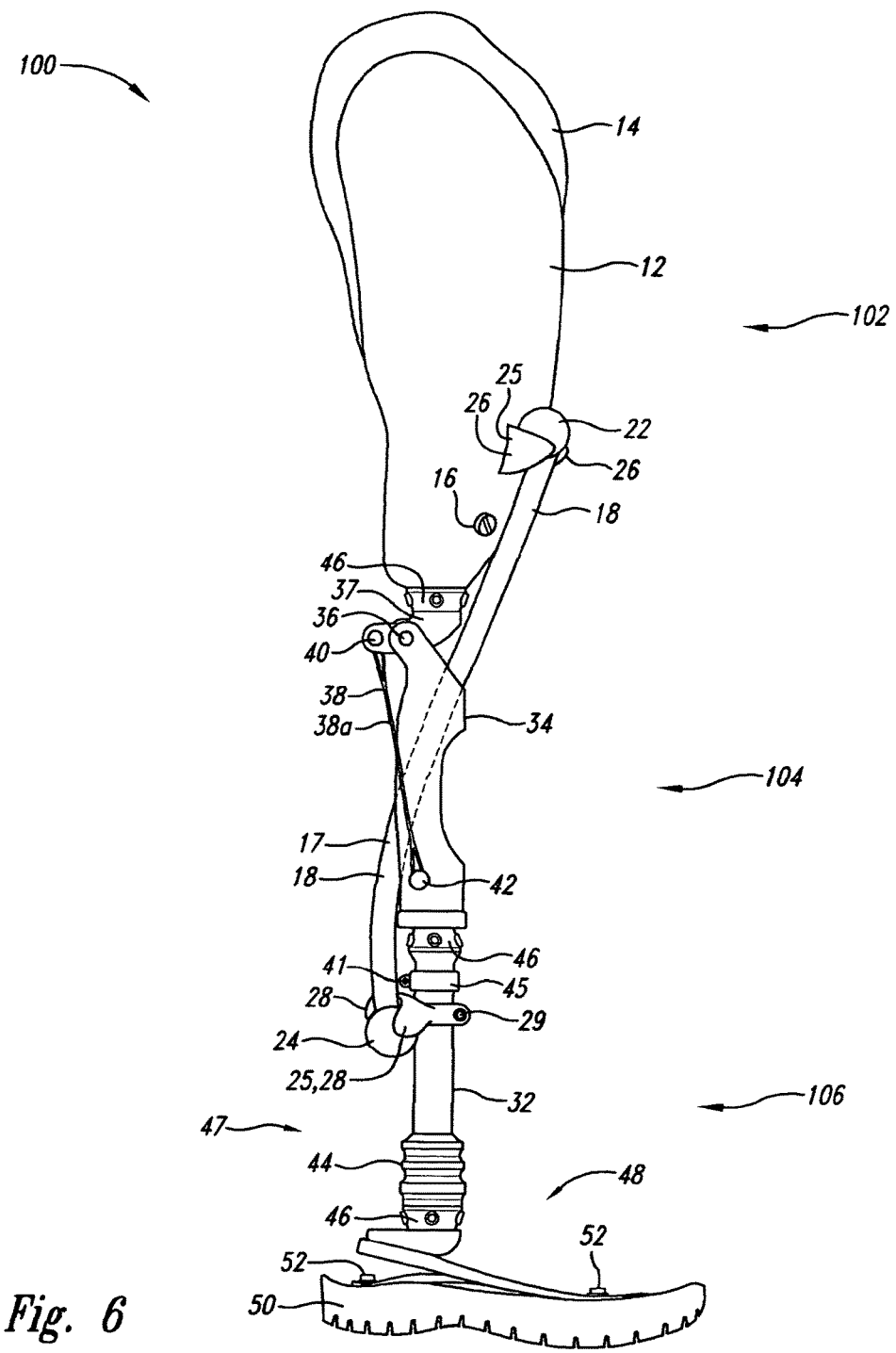
FIG. 6 is a right elevational view of an implementation of the prosthesis system depicted in FIG. 1.

The upper portion 102, used for coupling of the system 100 to the user's leg, may be comprised of an outer socket 12, an inner socket 14, and/or a shuttle lock 16, such as shown in FIG. 6. Further included in the upper portion 102 may be one or more elastic member retainer(s) 25, such as shown in FIG. 1.

The joint portion 104 of the system 100 may be comprised of one or more pyramid adapter(s) 46, a knee joint 37, a knee frame 34, a knee fulcrum 36, an adjustable anti-hyperextension member 38, an upper attachment point 40, and/or a lower attachment point 42, such as shown in FIG. 6.

The lower portion 106 of the system 100 may be comprised of a coupler 45 for coupling the middle portion 104 to the lower portion 106, a coupler clamp 41, one or more elastic member retainer(s) 25 and 28, a pylon 32, an ankle segment 47, and/or a foot 48. The ankle segment 47 may further encompass a pyramid adapter 46 and/or a resilient ankle joint 44. The resilient ankle joint, allowing a three-dimensional movement of the foot 48 relative to the lower portion 106, will deter any torsional and/or lateral forces being transferred from the foot to the user. This can help alleviate stress on the user's body, and may reduce the potential for injury to the user. The foot 48 may be comprised of a shoe 50 and/or any number of shoe fastener(s) 52. Additionally, the shoe 50 may be removed from the foot 48 via the fastener(s) 52, providing the ability to change the shoe in order to suit any number of various activities such as bicycling, skiing, surfing, snowboarding, and so forth.

Additionally, incorporated into the system 100 is one or more elastic members 18. The elastic member(s) are composed of a resilient material having a middle portion 17 with a decided level of elasticity for storing and releasing energy. The user chooses an elastic member 18 based on it's level of elasticity, the activity for which it will be used in, and according to his or her body weight. It should be noted that a higher level of elasticity would store and release more energy than a lower level of elasticity. The overall length and level of elasticity of the elastic member 18 determines the preloaded tension on the system. Further adjusting of the preload tension of the elastic member(s) 18 can be derived by positioning the lower ball retainer 28 along the longitudinal axis of the pylon 32, via a retainer adjusting element 29.

On opposing longitudinal ends of the elastic member 18 are an upper retaining ball 22 and a lower retaining ball 24, both of which may be comprised of a harder material than the middle portion 17, thereby hindering deformation of the retaining balls 22 and 24 while being retained in the ball retainers 25. Mounting of the elastic member(s) 18 to the system is accomplished via an upper ball retainer 26 and a lower ball retainer 28 located on the upper portion 102 and lower portion 106, respectively, which accept the retaining balls 22 and 24, respectively. Furthermore, alternative mounting locations of the retaining balls 22 and 24 can be derived by determining the locations of the ball retainers 25. The retaining balls 22 and 24 stay secured in the ball retainers 25 through the existing preload tension of the elastic member 18.

Routing of the elastic member(s) 18 can take the form of various configurations described herein.

Two or more elastic members 18 may be mounted to the lower portion 106 via lower ball retainers 28, having the middle portions 17 routed through the knee frame 34 of the joint portion 104, and mounted to the upper portion 102 via upper ball retainers 26, such as shown in FIG. 1.

Figure 9:
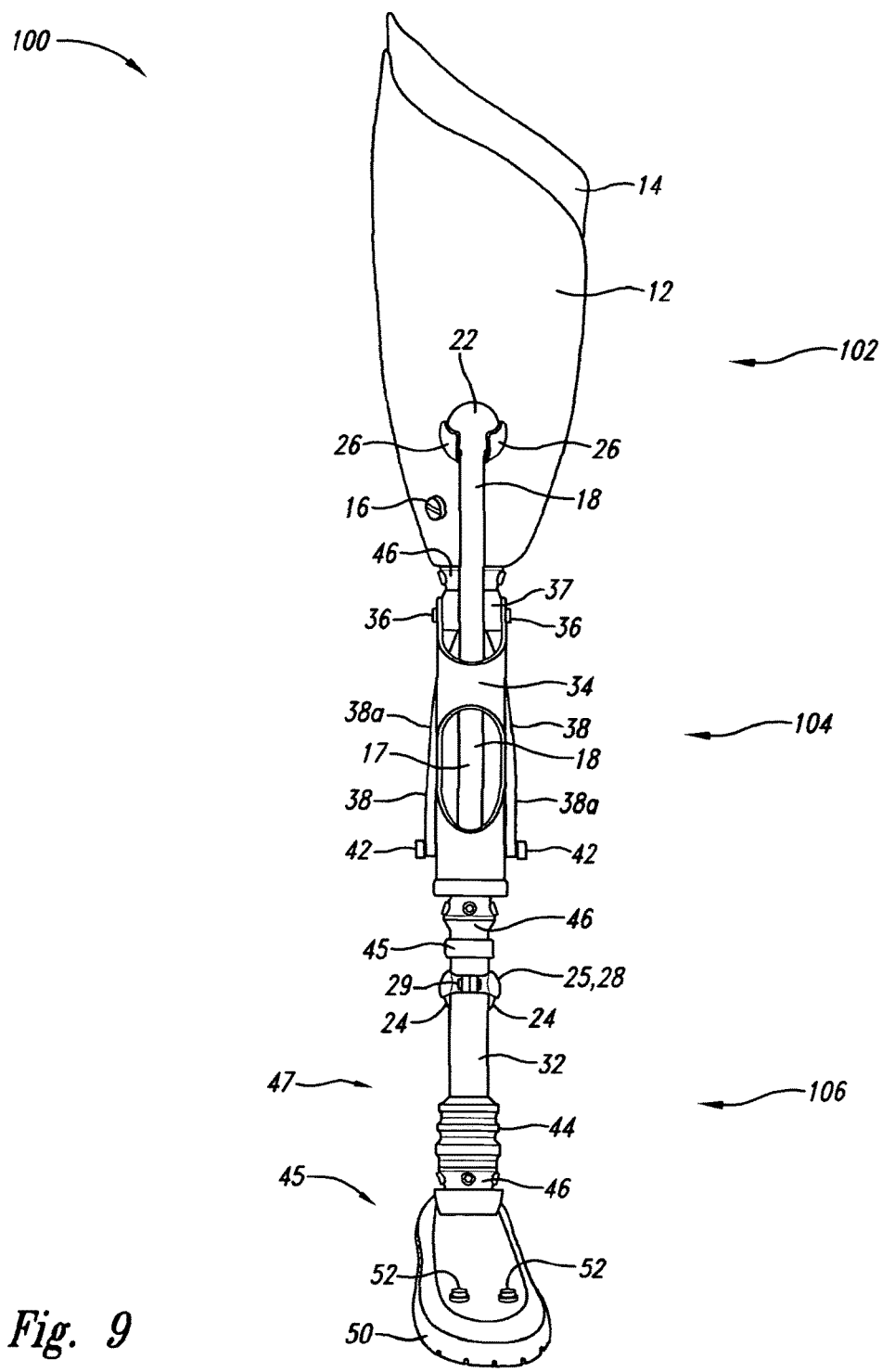
FIG. 9 is a front elevational view of an alternative implementation of a prosthesis system shown in the resting position, having one elastic member routed through the knee frame, and shown with an adjustable strap acting as an anti-hyperextension member.
Figure 10:
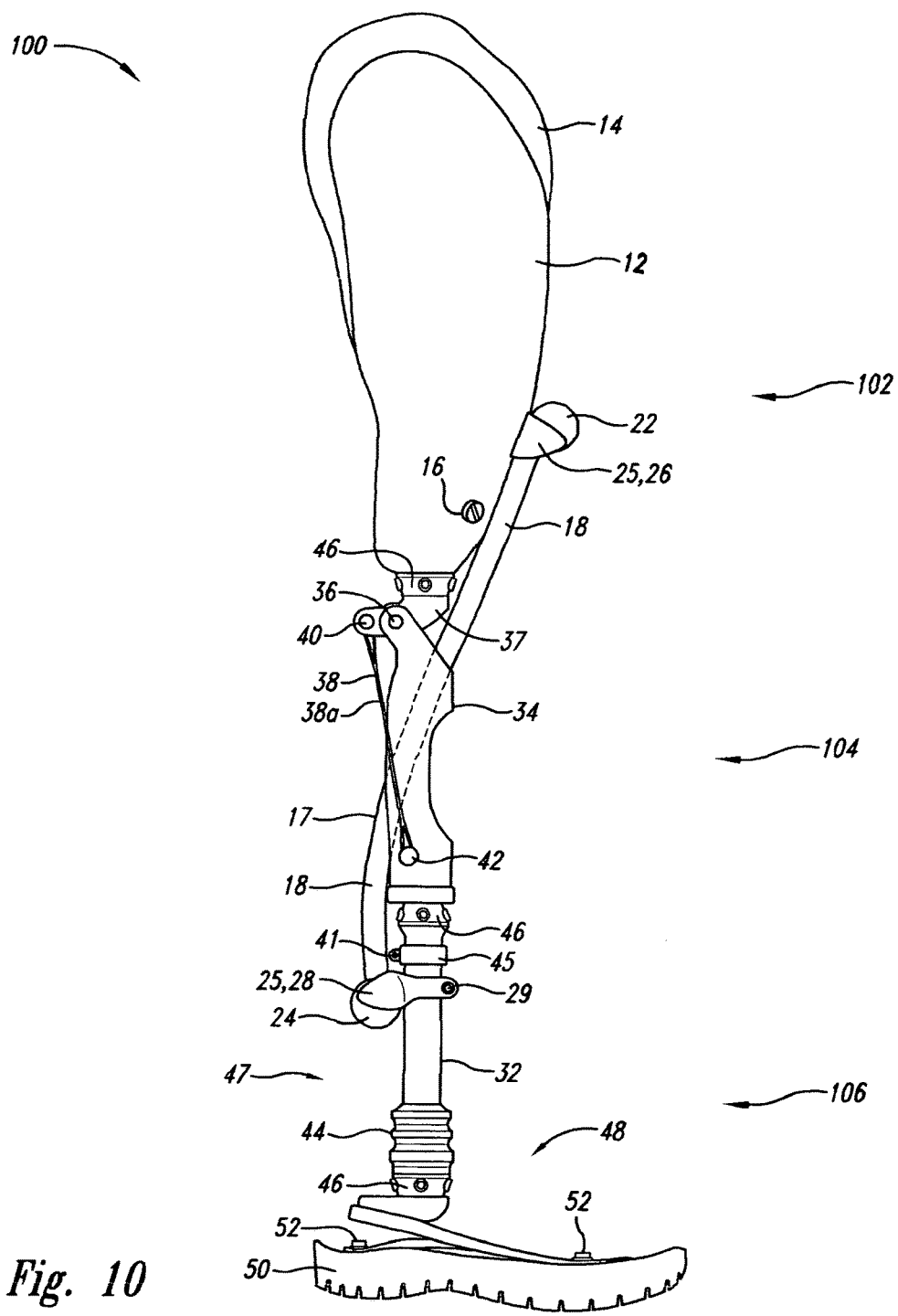
FIG. 10 is a right elevational view of an implementation of the prosthesis system depicted in FIG. 9.

One elastic member 18 may be mounted to the lower portion 106 via a lower ball retainer 28, having the middle portion 17 routed through the knee frame 34 of the joint portion 104, and mounted to the upper portion 102 via an upper ball retainer 26, such as shown in FIG. 9.

Figure 11:
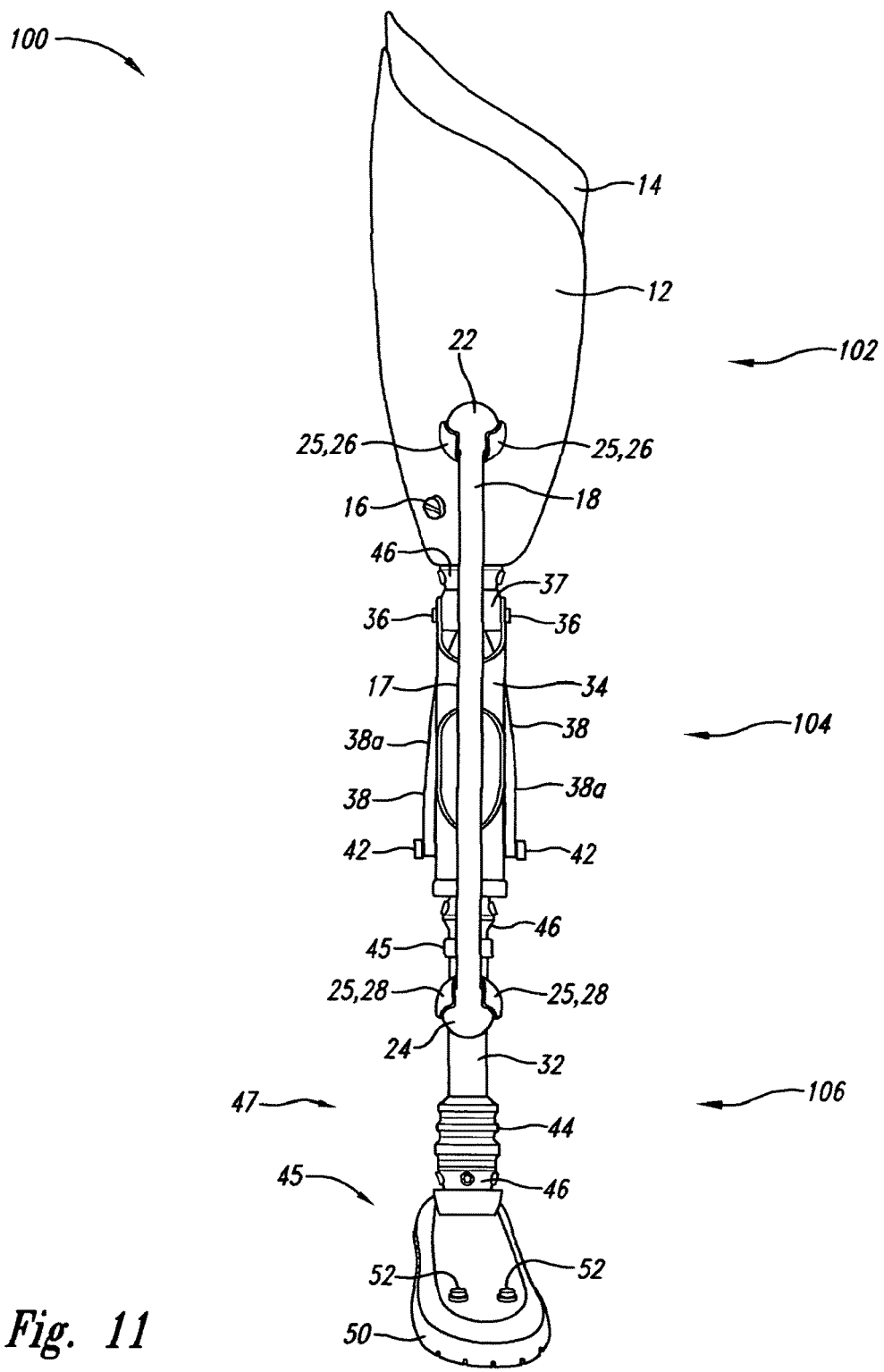
FIG. 11 is a front elevational view of an alternative implementation of a prosthesis system shown in the resting position, having one elastic member frontally routed, and shown with an adjustable strap acting as an anti-hyperextension member.
Figure 12:
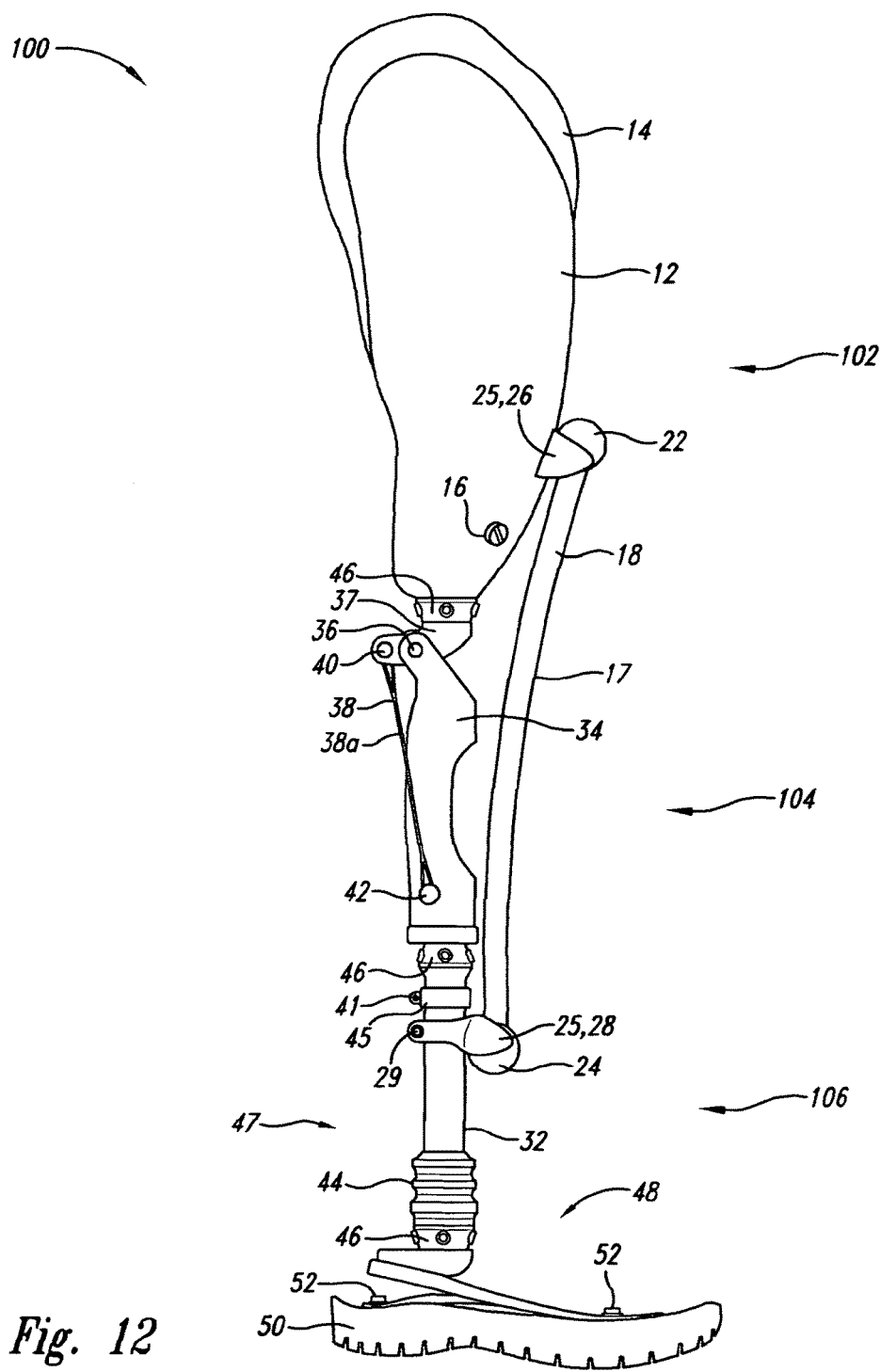
FIG. 12 is a right elevational view of an implementation of the prosthesis system depicted in FIG. 11.
Figure 13:
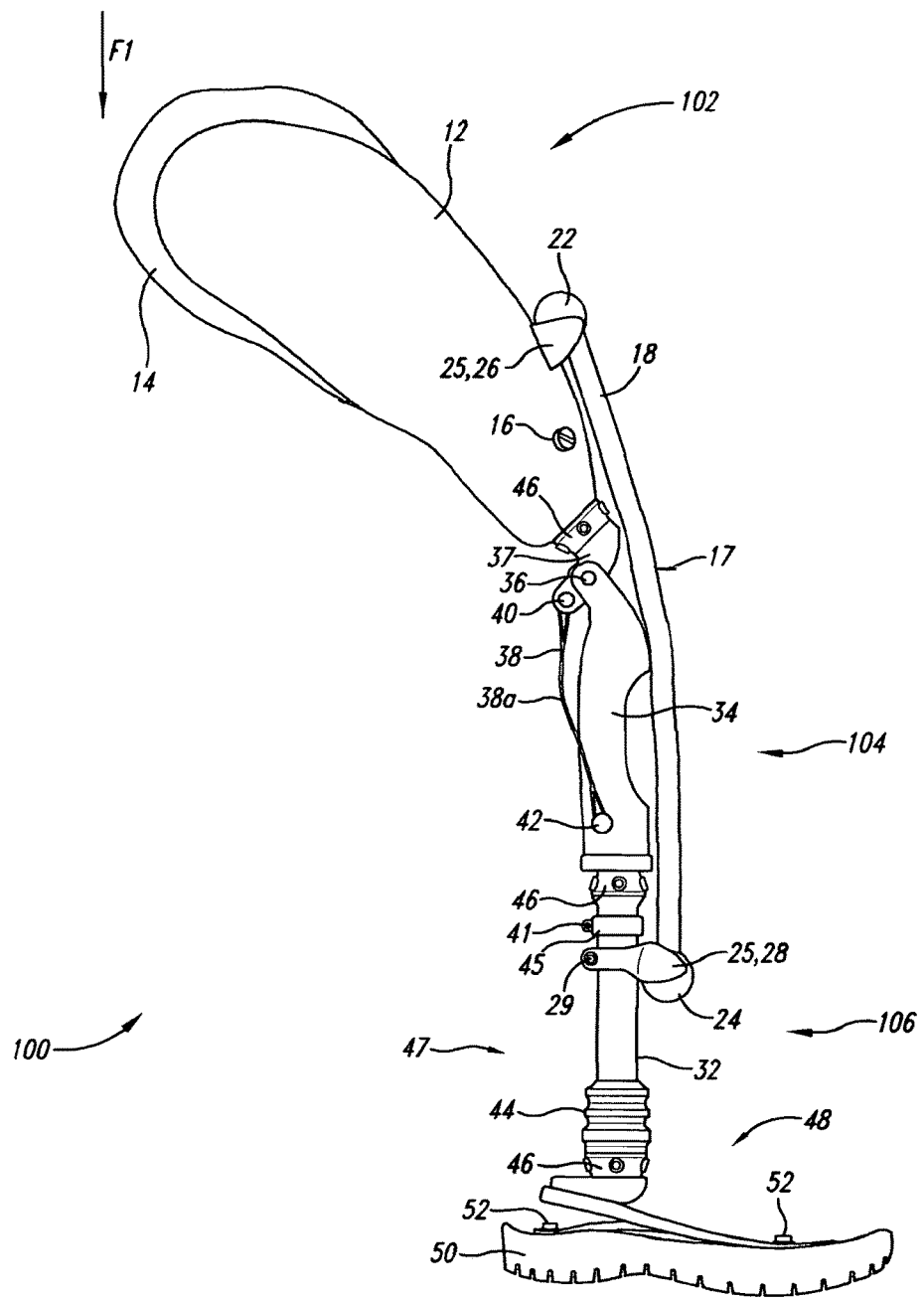
FIG. 13 a right elevational view of an implementation of the same prosthesis system depicted in FIG. 11, but alternately shown in a forty-five degree bent position.
Figure 14:
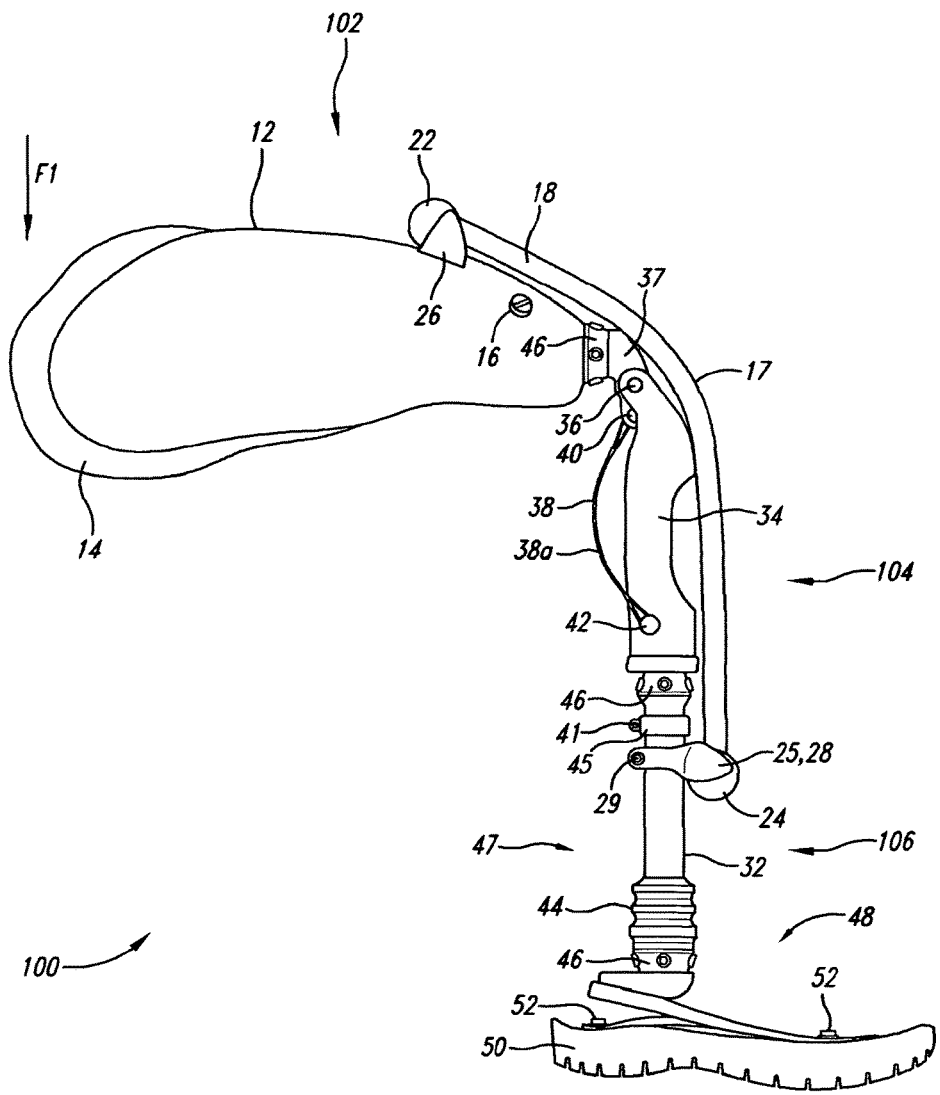
FIG. 14 is a right elevational view of an implementation the same prosthesis system depicted in FIG. 11, but alternately shown in a ninety degree bent position.

One elastic member 18 may be mounted to the lower portion 106 via a lower ball retainer 28, having the middle portion 17 routed frontally across the knee frame 34 of the joint portion 104, and mounted to the upper portion 102 via an upper ball retainer 26, such as shown in FIG. 11.

Figure 15:
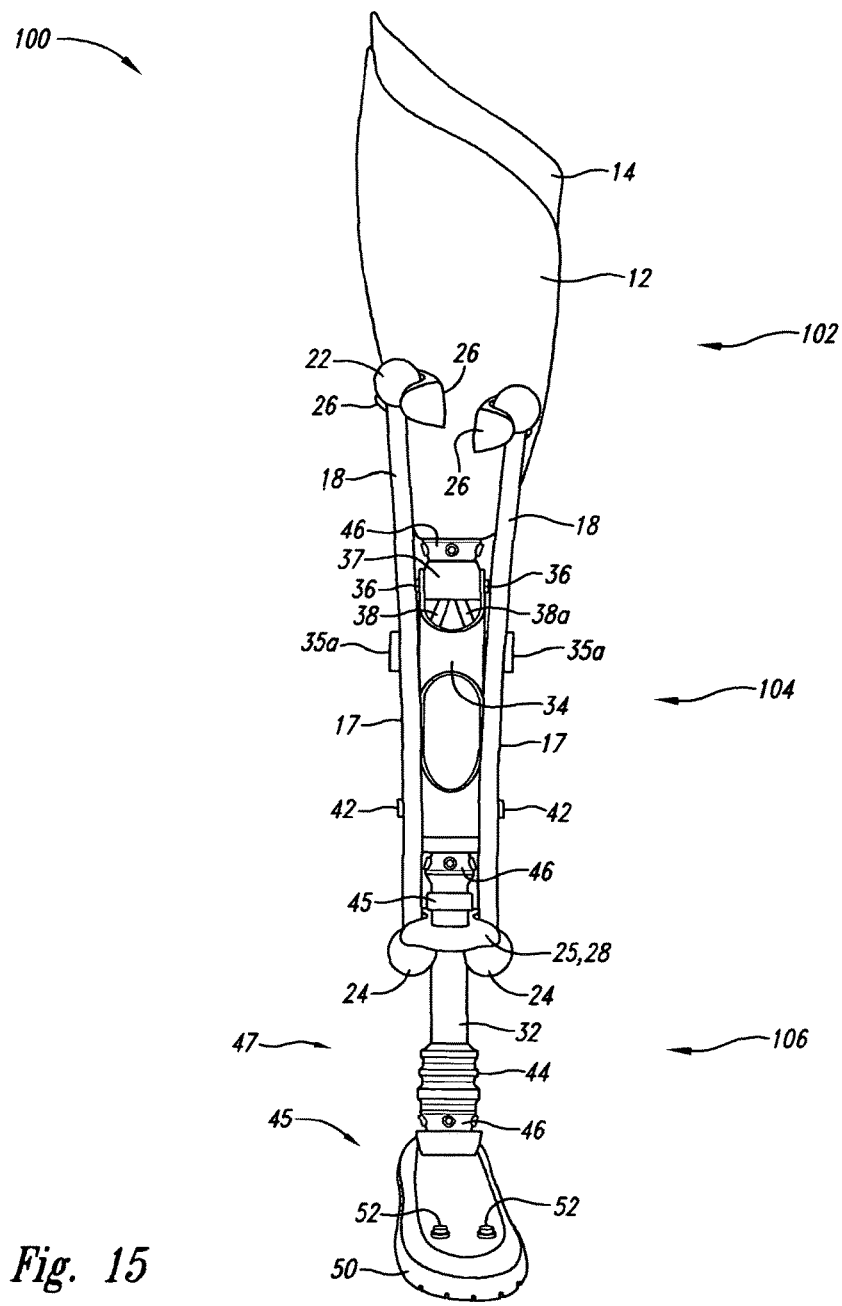
FIG. 15 is a front elevational view of an alternative implementation of a prosthesis system shown in the resting position, having two elastic members frontally routed.
Figure 17:
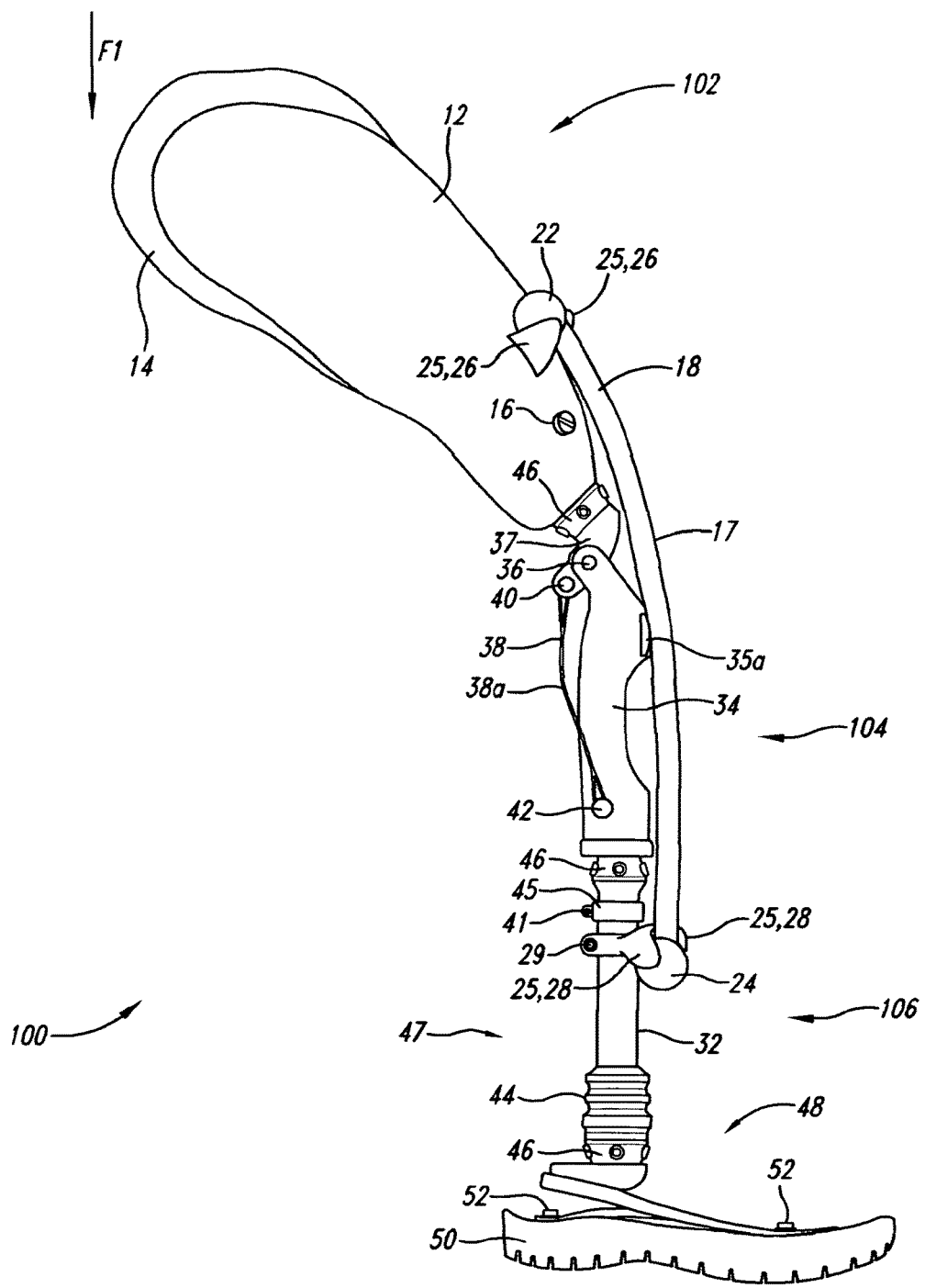
FIG. 17 is a right elevational view of an implementation of the same prosthesis system depicted in FIG. 15, but alternately shown in a forty-five degree bent position.
Figure 18:
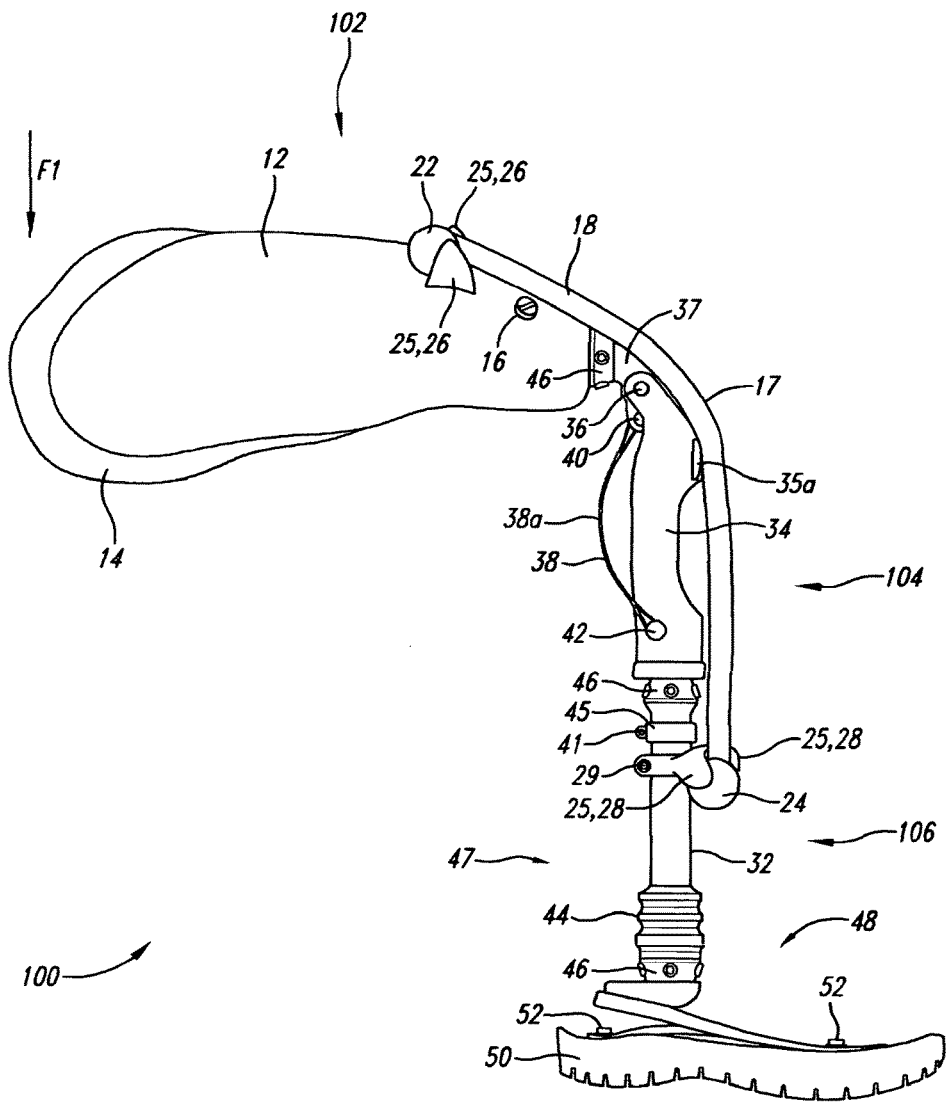
FIG. 18 is a right elevational view of an implementation of the same prosthesis system depicted in FIG. 15, but alternately shown in a ninety degree bent position.
Figure 19:
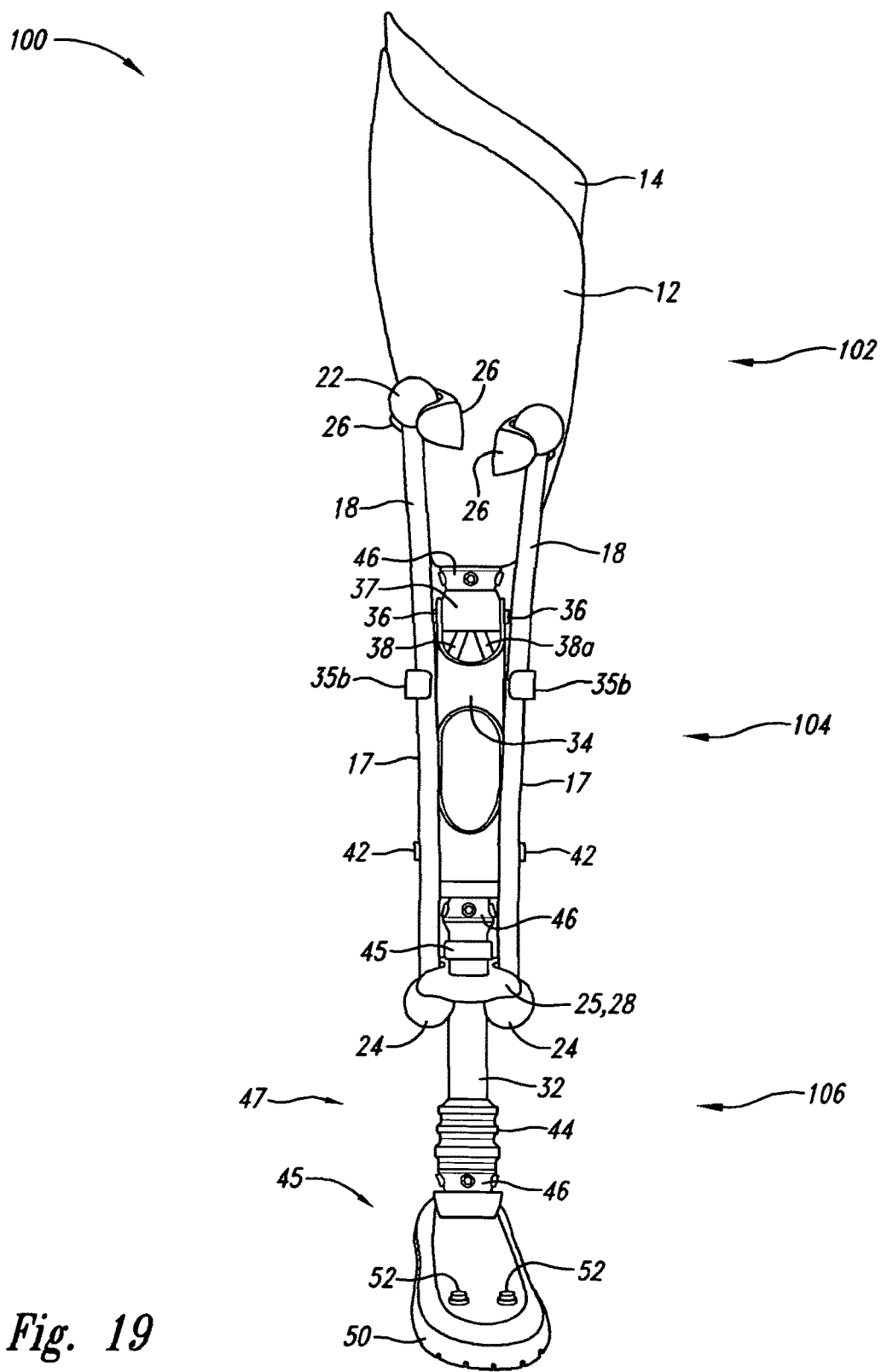
FIG. 19 is a front elevational view of an implementation of the same prosthesis system depicted in FIG. 15, but alternately shown with a hook style elastic member retainer.
Figure 20:
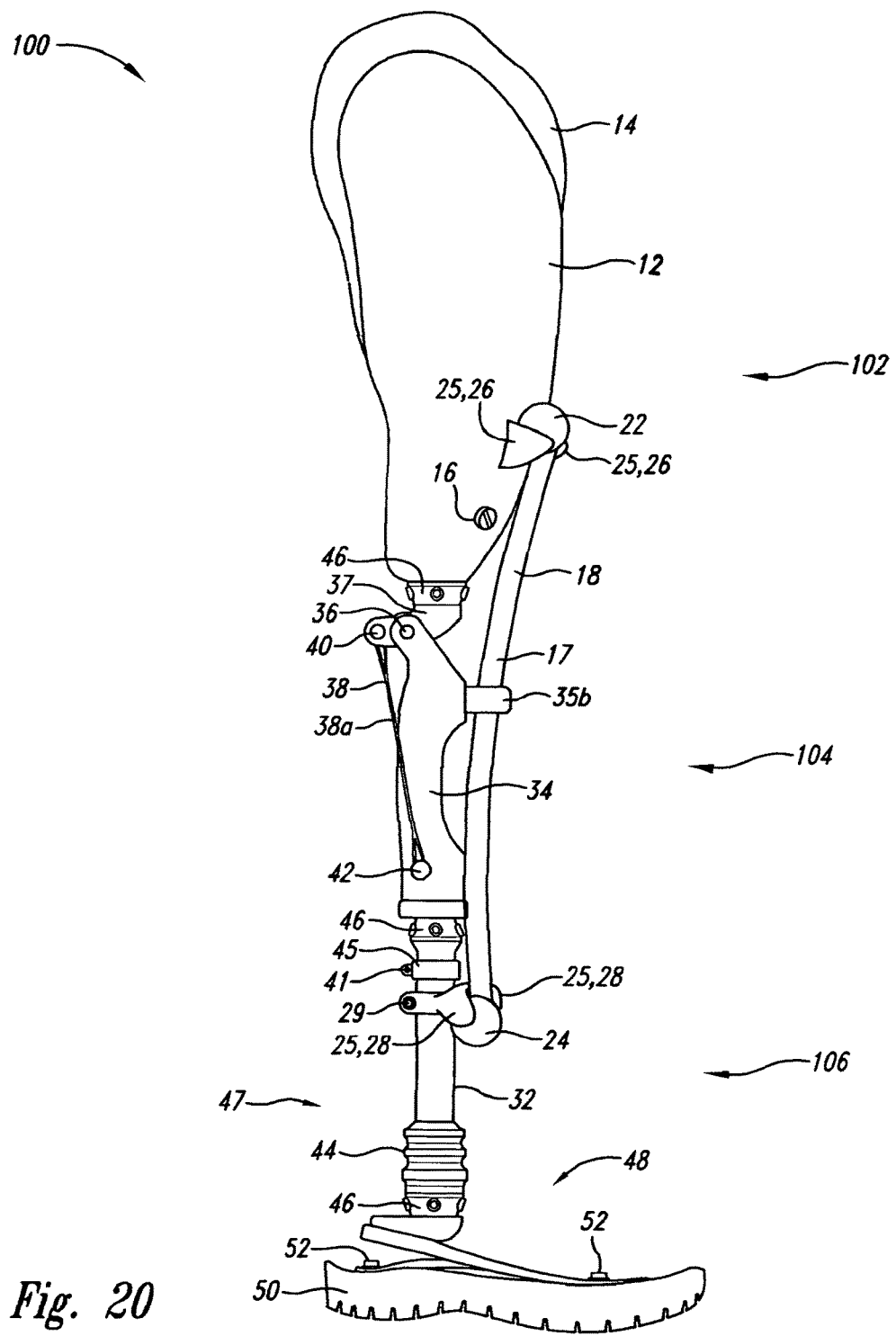
FIG. 20 is a right elevational view of an implementation of the same prosthesis system depicted in FIG. 20.

Two or more elastic members 18 may be mounted to the lower portion 106 via lower ball retainers 28, having the middle portions 17 routed frontally across the knee frame 34 of the joint portion 104, and mounted to the upper portion 102 via upper ball retainers 26, such as shown in FIG. 15. In this implementation it may be necessary to incorporate an elastic member retaining element 35 for supporting the middle portion 17 of the elastic member 18. The retaining element 35*a* may be configured as a simple seat, such as shown in FIGS. 15, 16, 17, and 18, or alternately configured as a hook type element 35*b* for a more secure retention of the middle portion 17, such as shown in FIGS. 19 and 20.

Figure 7:
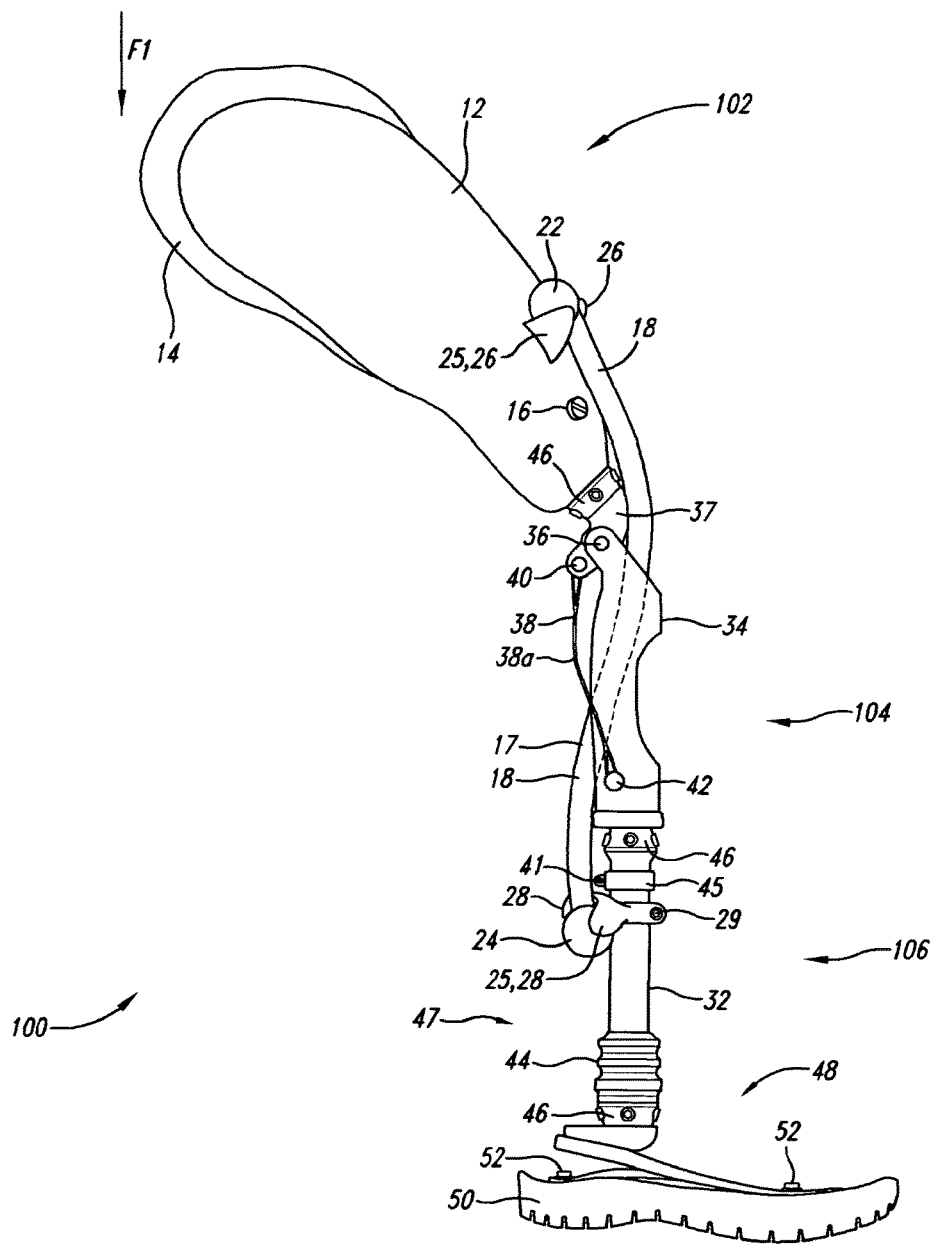
FIG. 7 is a right elevational view of an implementation of the same prosthesis system depicted in FIG. 1, but alternately shown in a forty-five degree bent position.
Figure 8:
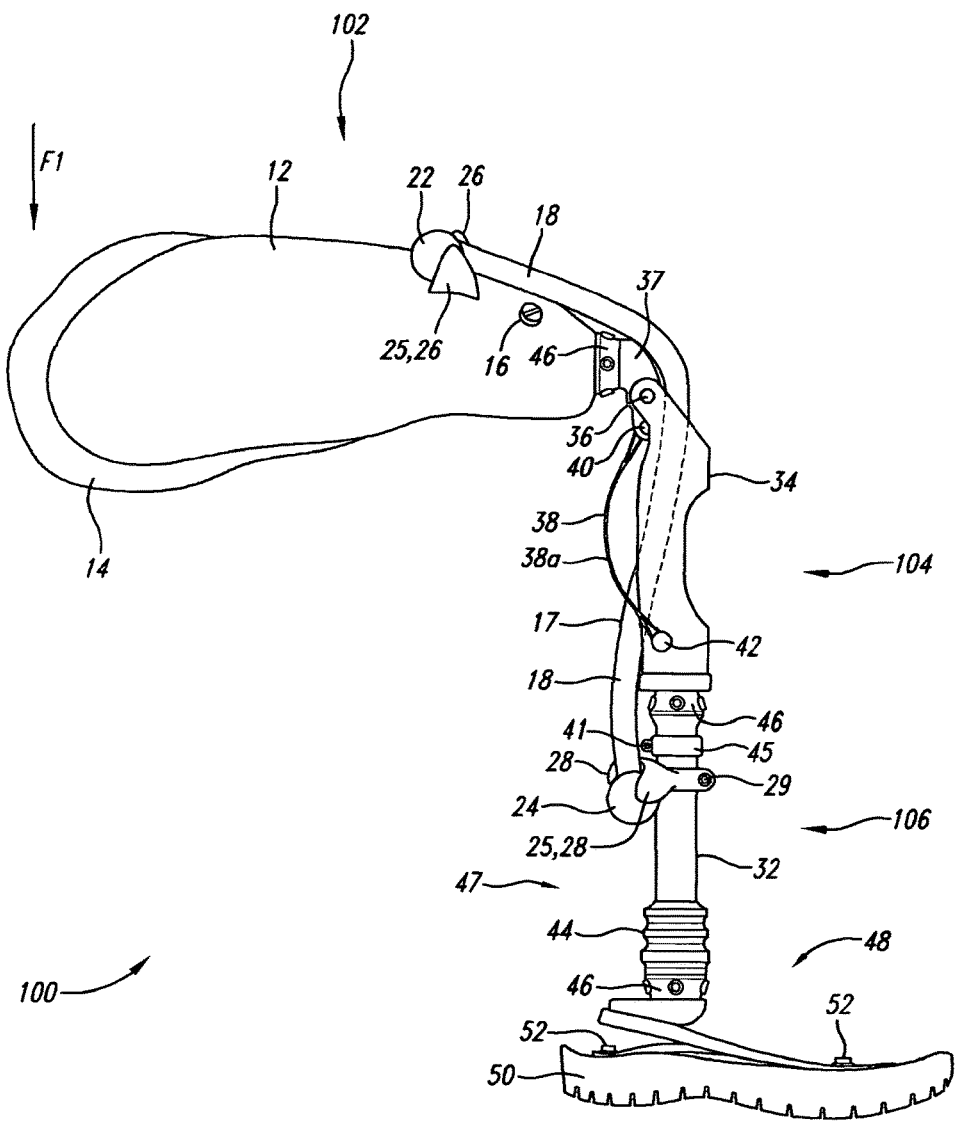
FIG. 8 is a right elevational view of an implementation of the same prosthesis system depicted in FIG. 1, but alternately shown in a ninety degree bent position.

By allowing the user to apply the force F1 of his or her own body weight, the system seeks a bent position. In other words, the upper portion 102 rotates around the knee fulcrum 36 and down towards the lower portion 106, as shown if FIGS. 7 and 8. This may in some respects mimic the bending of a knee. While in a bent position the elastic member(s) 18 are further stressed and applying a tensional force between the upper portion 102 and lower portion 106, such as shown in FIGS. 7 and 8. The tensional force applied by the elastic member(s) 18 will return the system to a resting position when the force F1 of the user's body weight is diminished or removed, such as shown in FIG. 6. In some respects this may mimic the function of the quadriceps muscles of the leg, acting as an extensor.

Figure 16:
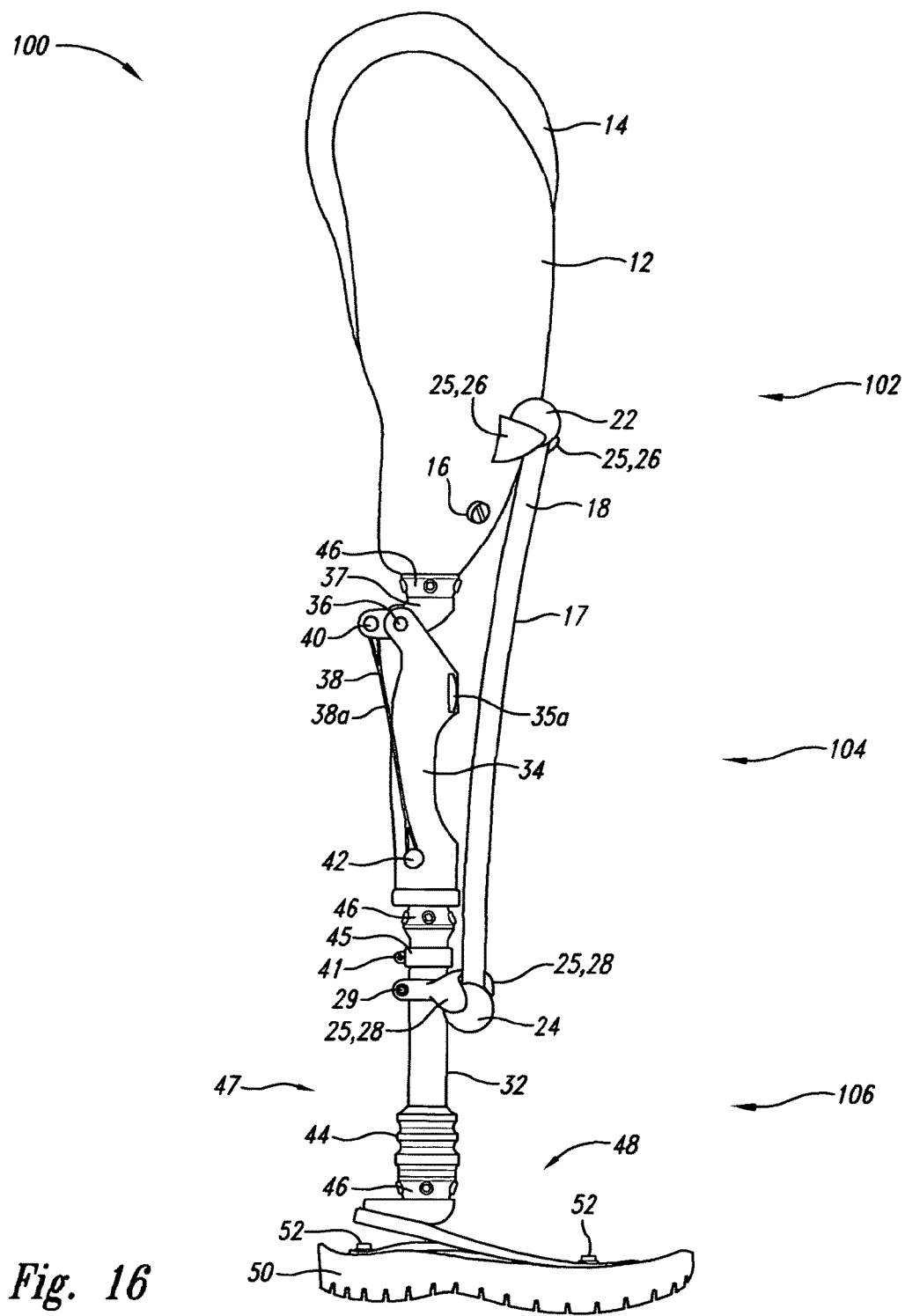
FIG. 16 is a right elevational view of an implementation of the prosthesis system depicted in FIG. 15, and shown with an adjustable strap acting as an anti-hyperextension member.
Figure 21:
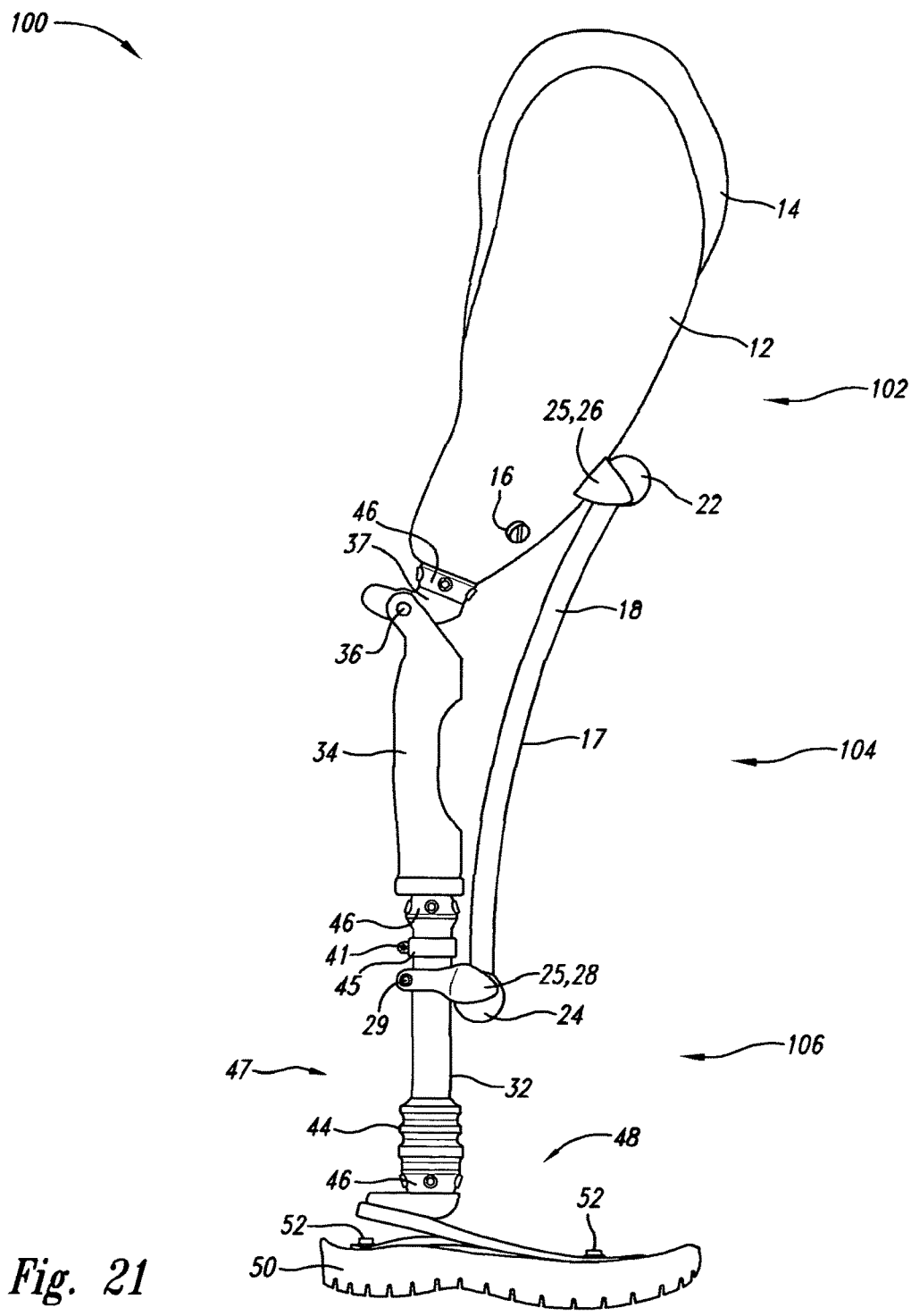
FIG. 21 is a right elevation view of a prosthesis system in a hyper extended state, and lacking an anti-hyperextension member.
Figure 22:
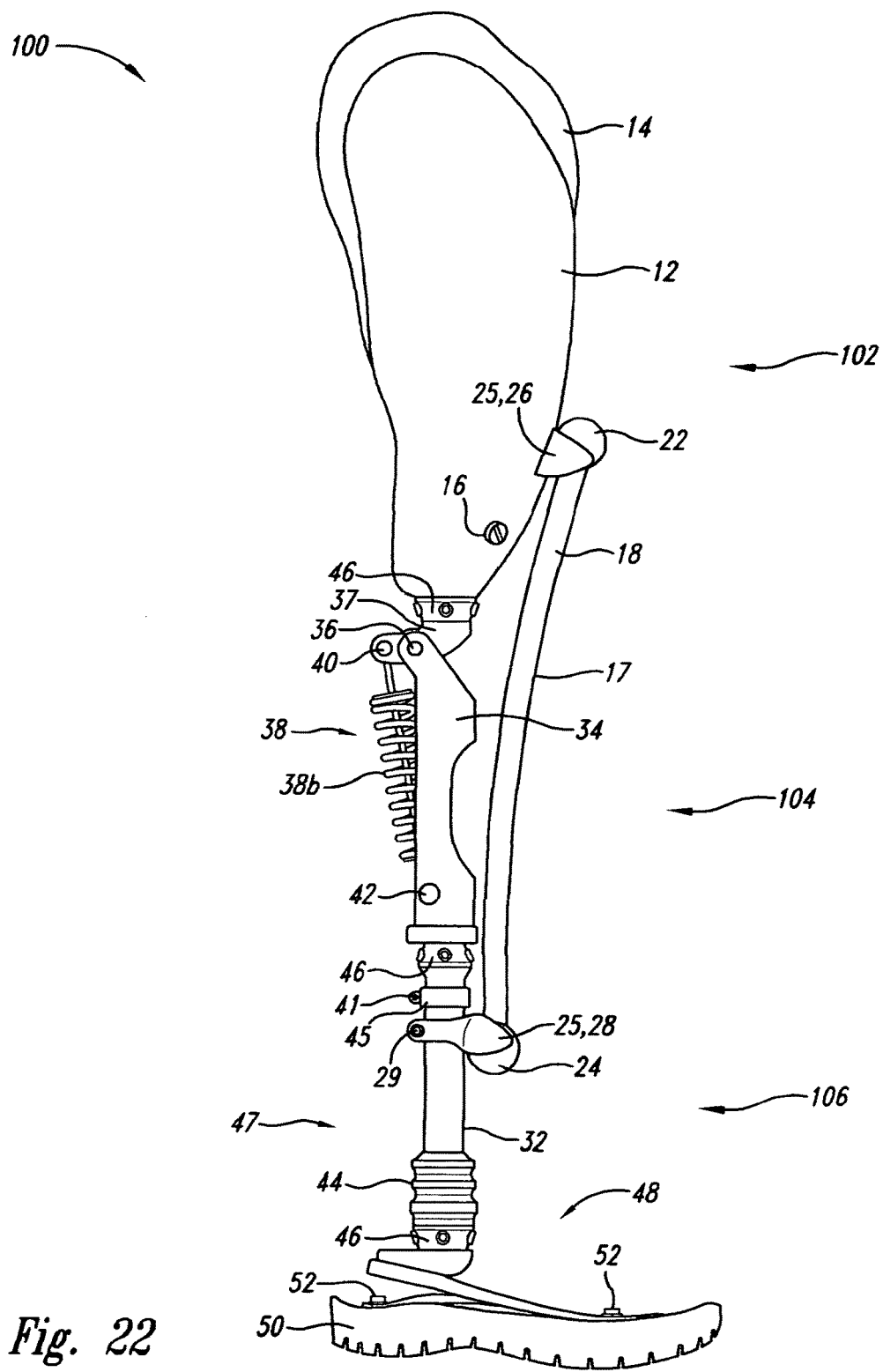
FIG. 22 is a right elevational view of an alternative implementation of the prosthesis system depicted in FIG. 15, but alternately shown with an adjustable tension spring acting as an anti-hyperextension member.
Figure 23:
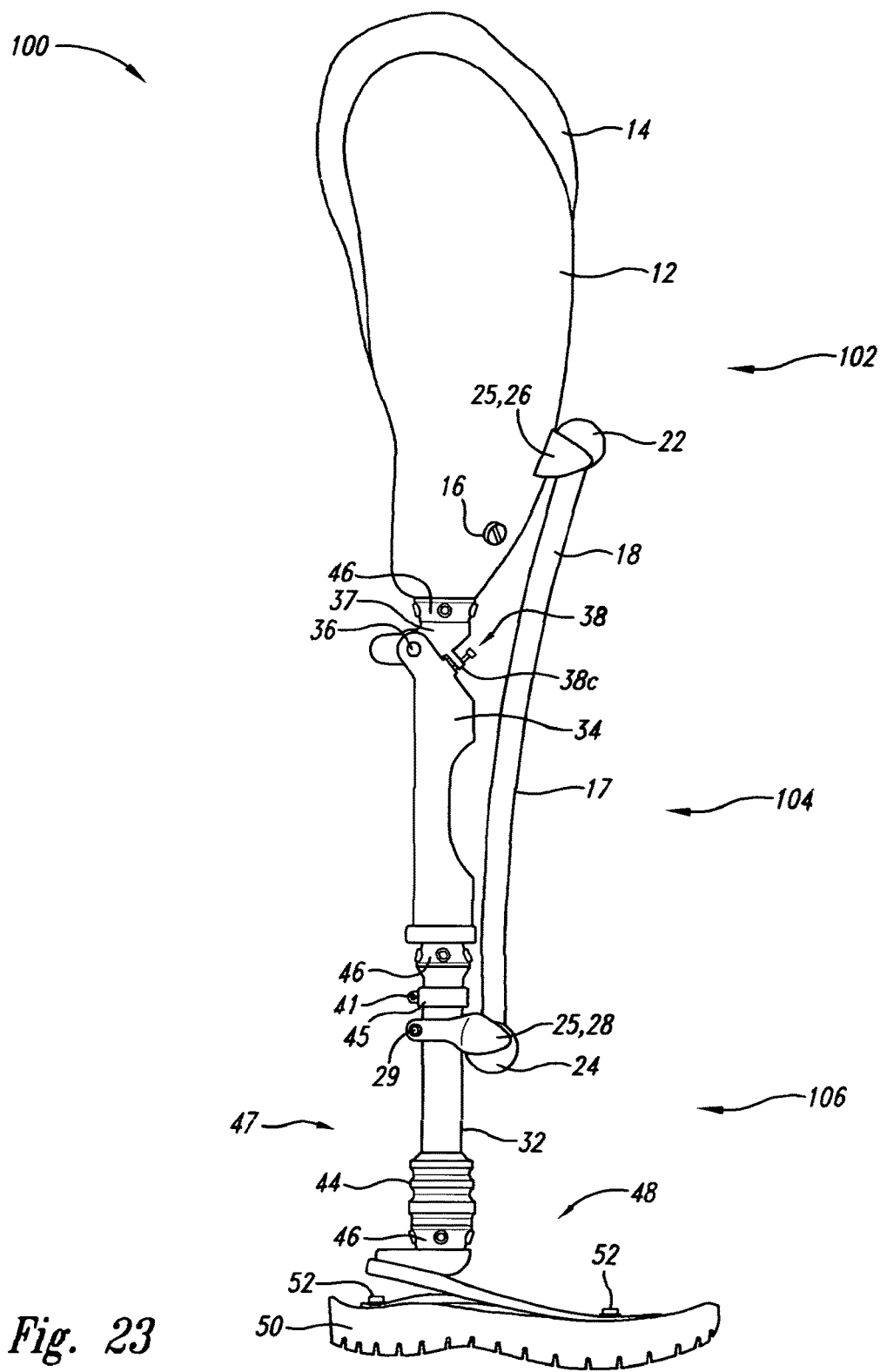
FIG. 23 is a right elevational view of an alternative implementation of the prosthesis system depicted in FIG. 15, but alternately shown with an adjustable stop acting as an anti-hyperextension member.
Figure 24:
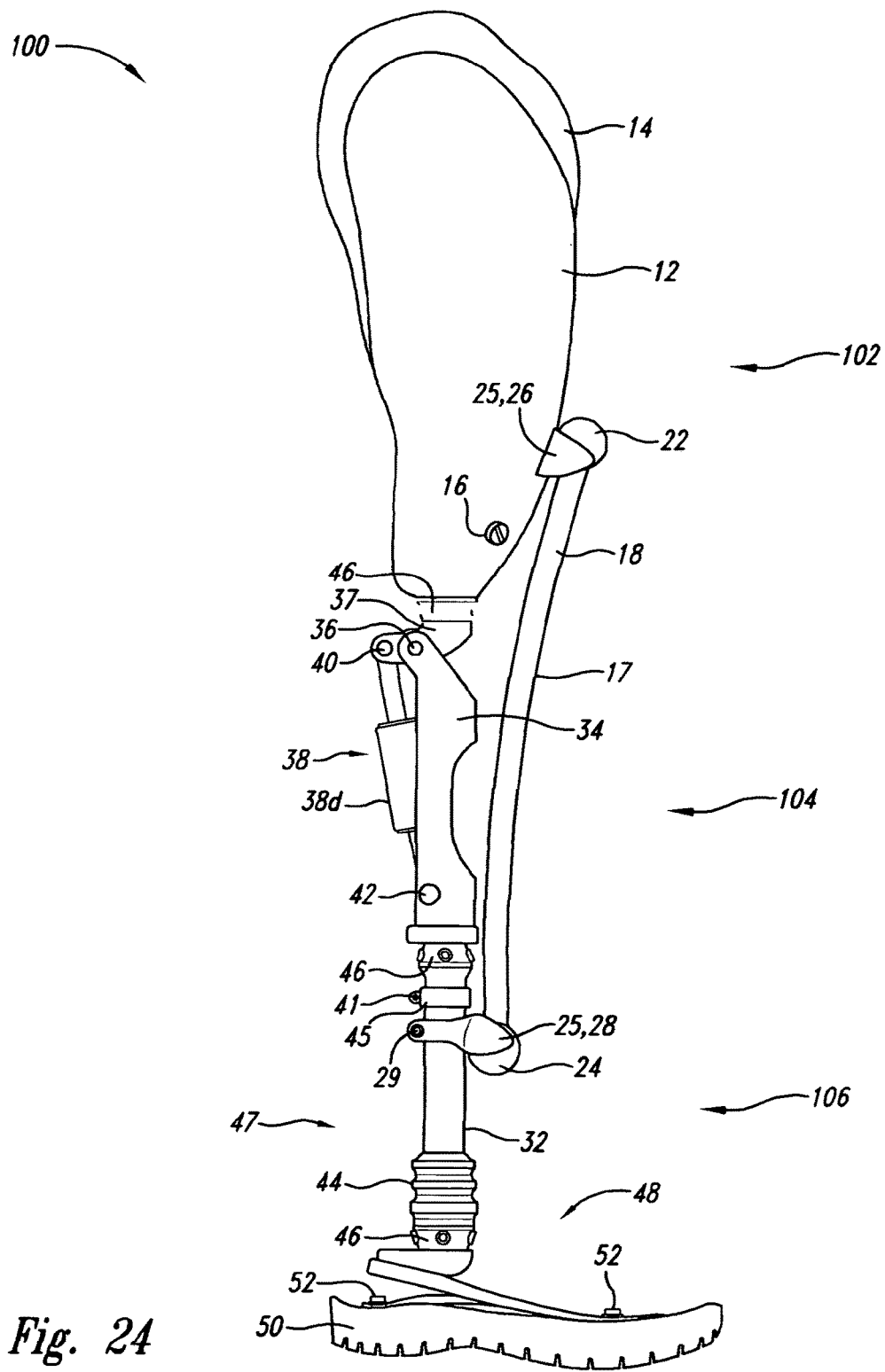
FIG. 24 is a right elevational view of an alternative implementation of the prosthesis system depicted in FIG. 15, but alternately shown with a fluidic shock absorber acting as an anti-hyperextension member.

The tensional force applied by the elastic member(s) 18 can cause the system 100 to hyperextend beyond the resting position, such as shown in FIG. 21. To prevent hyperextension, an adjustable anti-hyperextension member 38 may be integrated into the system 100. This can be mounted between an upper attachment point 40 and a lower attachment point 42 within the joint portion 104. The anti-hyperextension member 38 can also be adjusted so as to define the resting position of the system 100. A simple strap 38*a* made of a resilient or non-resilient material could be used as the acting anti-extension member 38, such as shown in FIGS. 16, 17, and 18, and could further include examples such as: an adjustable tension spring 38*b* such as shown in FIG. 22, an adjustable stop 38*c* such as shown in FIG. 23, and/or an adjustable fluidic shock absorber 38*d* such as shown in FIG. 24.

The ankle segment 47 may encompass a pyramid adapter 46 and/or a resilient ankle joint 44. The resilient ankle joint, allowing a three-dimensional movement of the foot 48 relative to the lower portion 106, will deter any torsional and/or lateral forces being transferred from the foot to the user. This can help alleviate stress on the user's body, and may reduce the potential for injury to the user.

Figure 25:
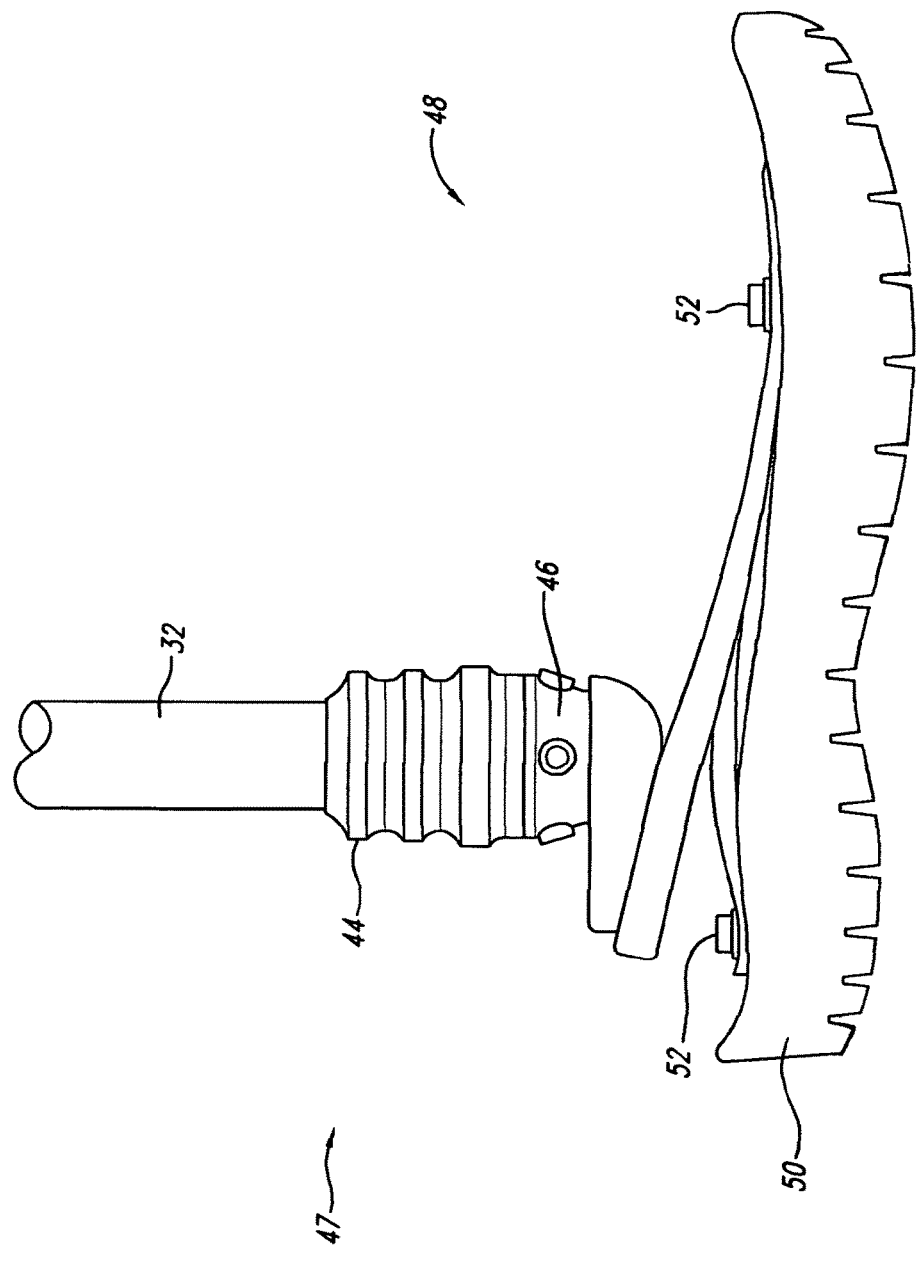
FIG. 25 is a right elevational view of an implementation of the foot portion having a standard shoe.
Figure 26:
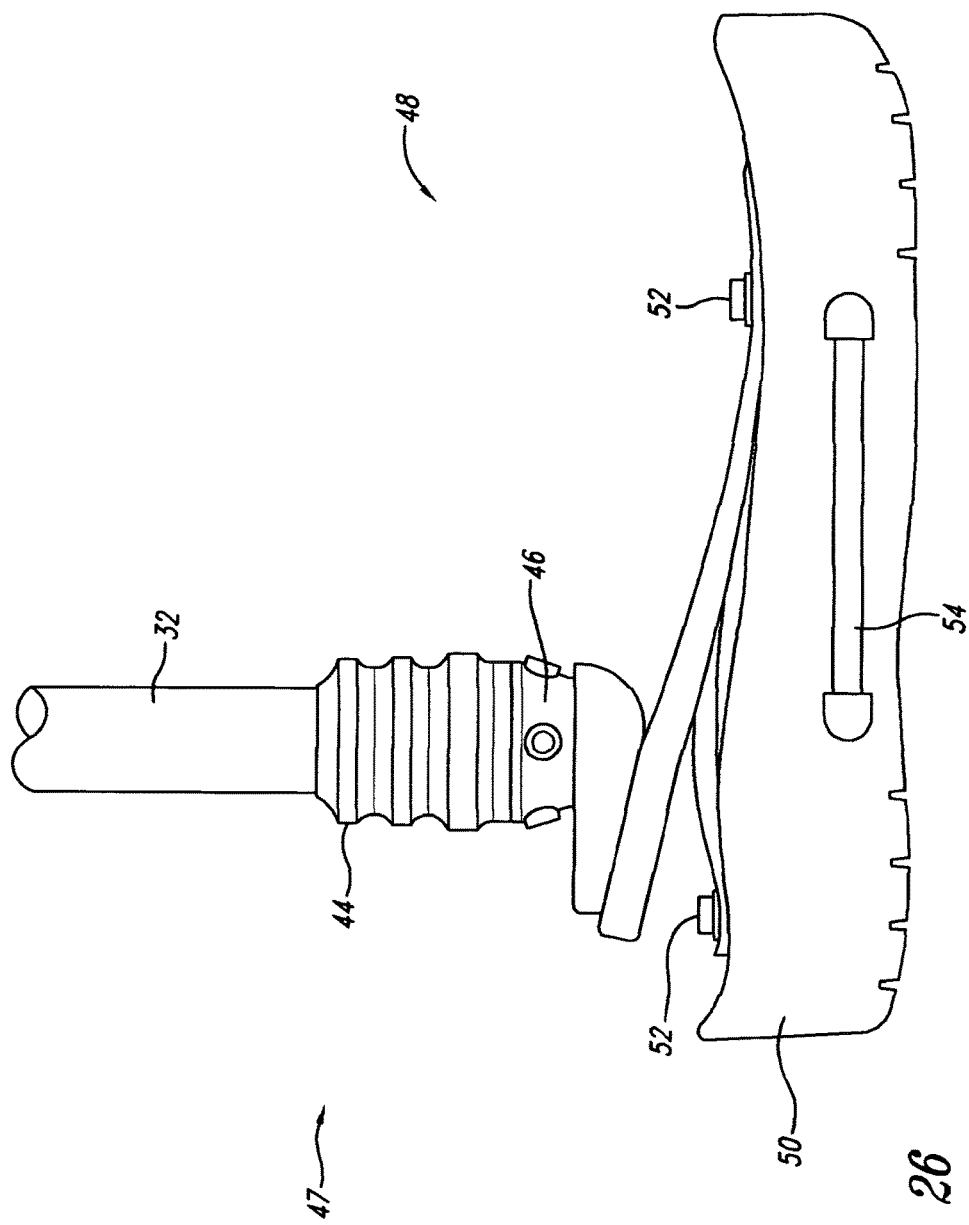
FIG. 26 is a right elevational view of an alternative implementation of the foot portion having a clip-in style snowboard and/or wakeboard shoe.
Figure 27:
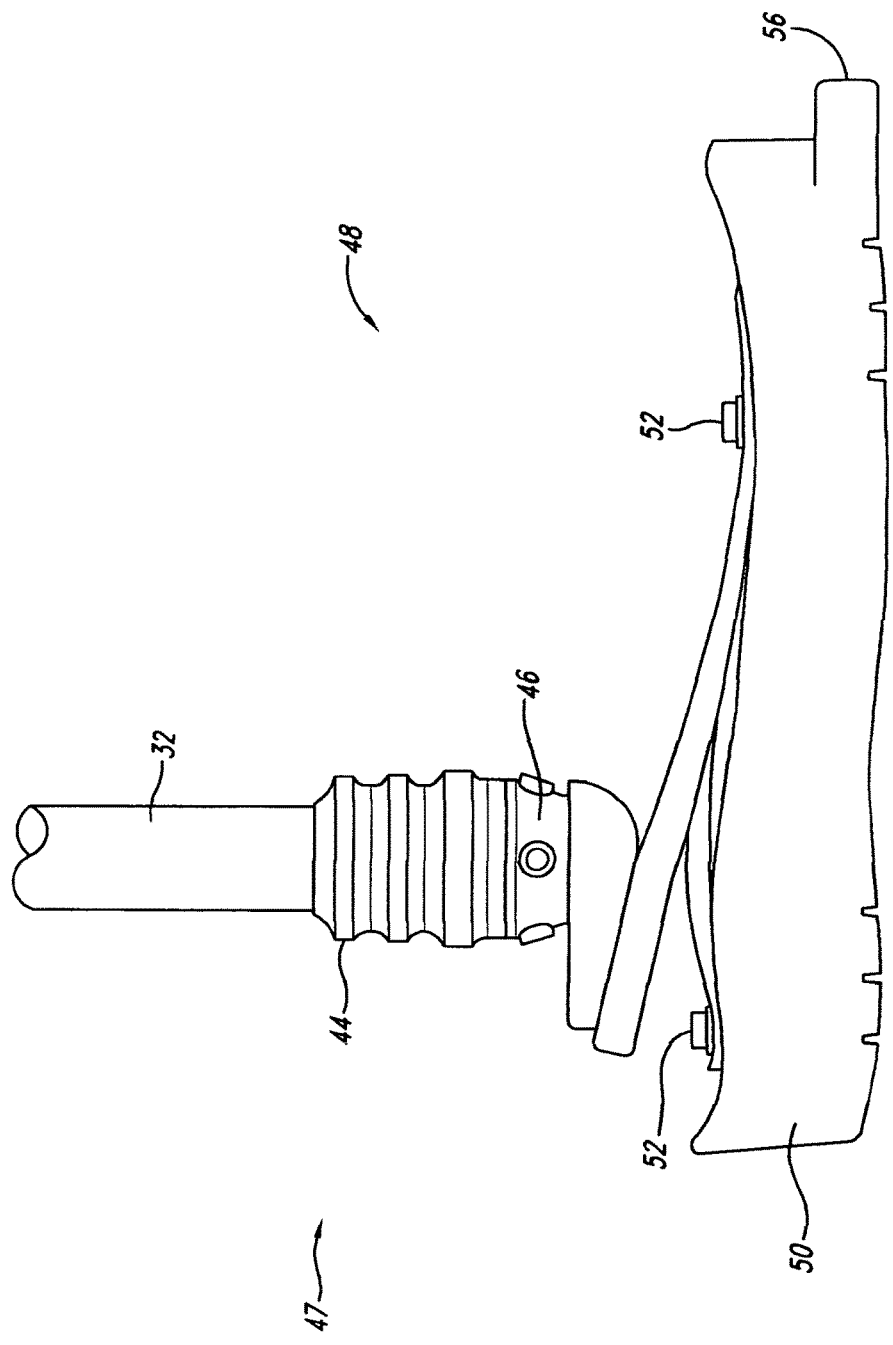
FIG. 27 is a right elevational view of an alternative implementation of the foot portion having a cross-country and/or telemarking shoe.
Figure 28:
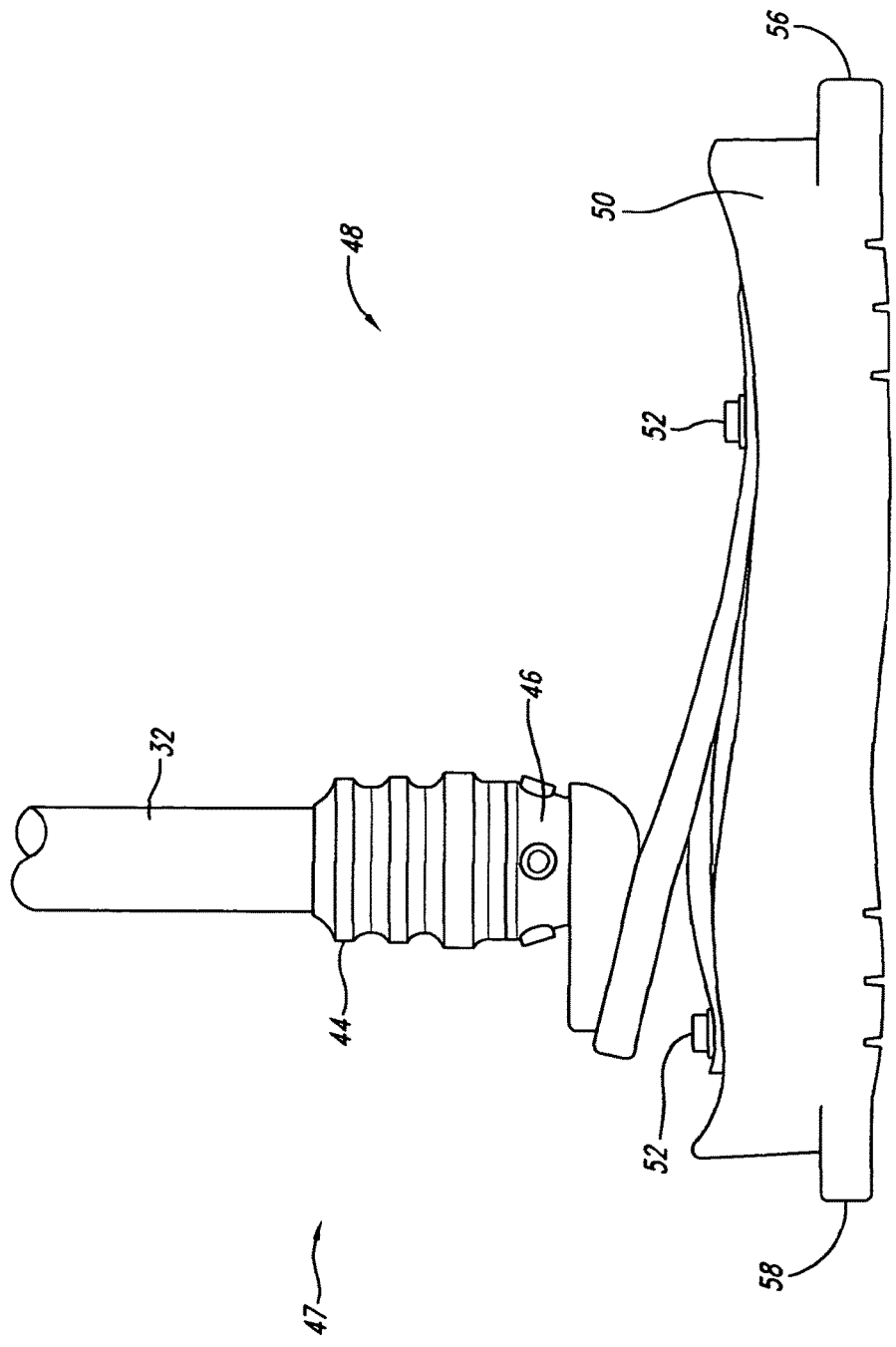
FIG. 28 is a right elevational view of an alternative implementation of the foot portion having a downhill snow ski shoe.
Figure 29:
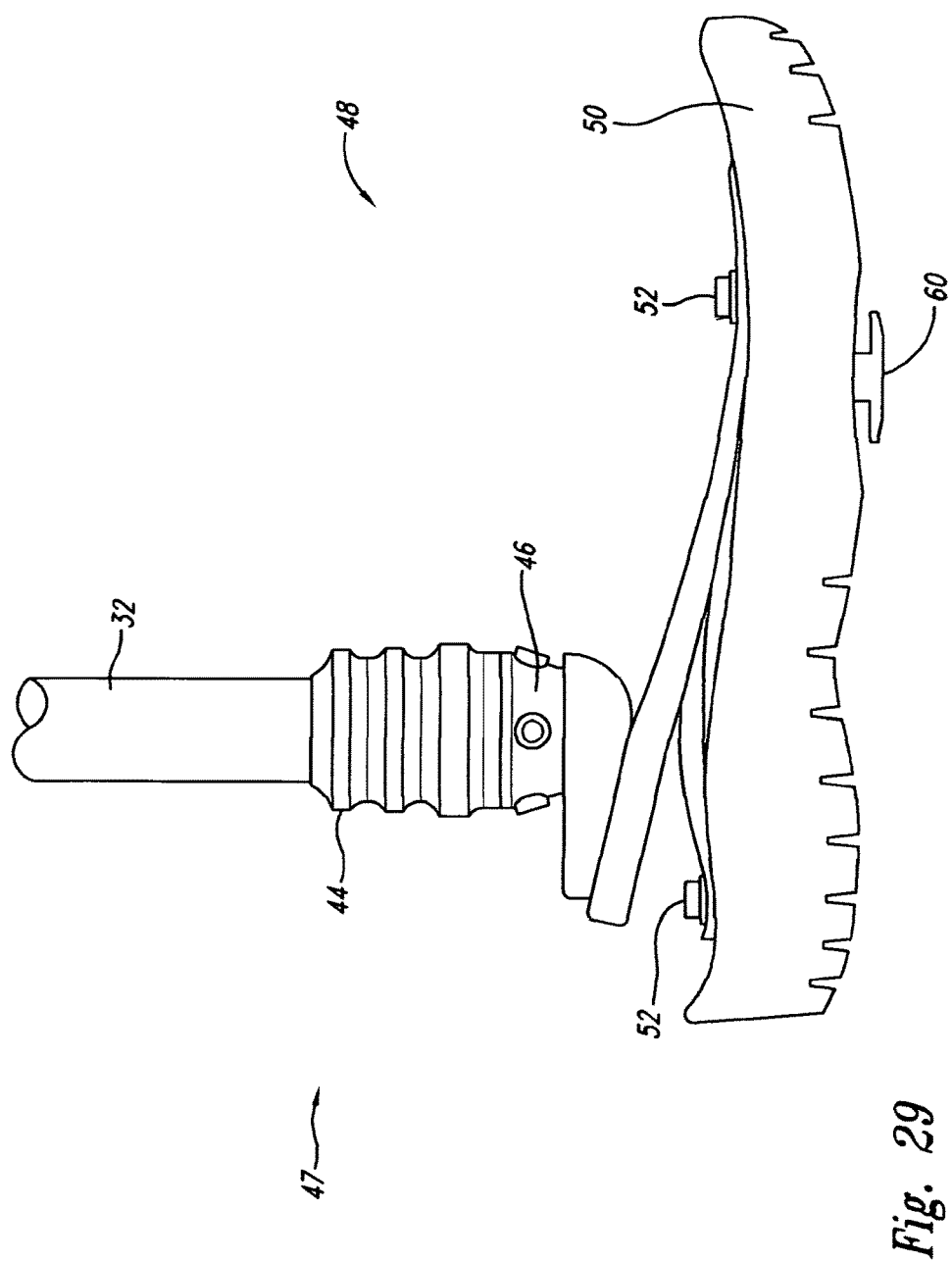
FIG. 29 is a right elevational view of an alternative implementation of the foot portion having a bicycle clipless type shoe.
Figure 30:
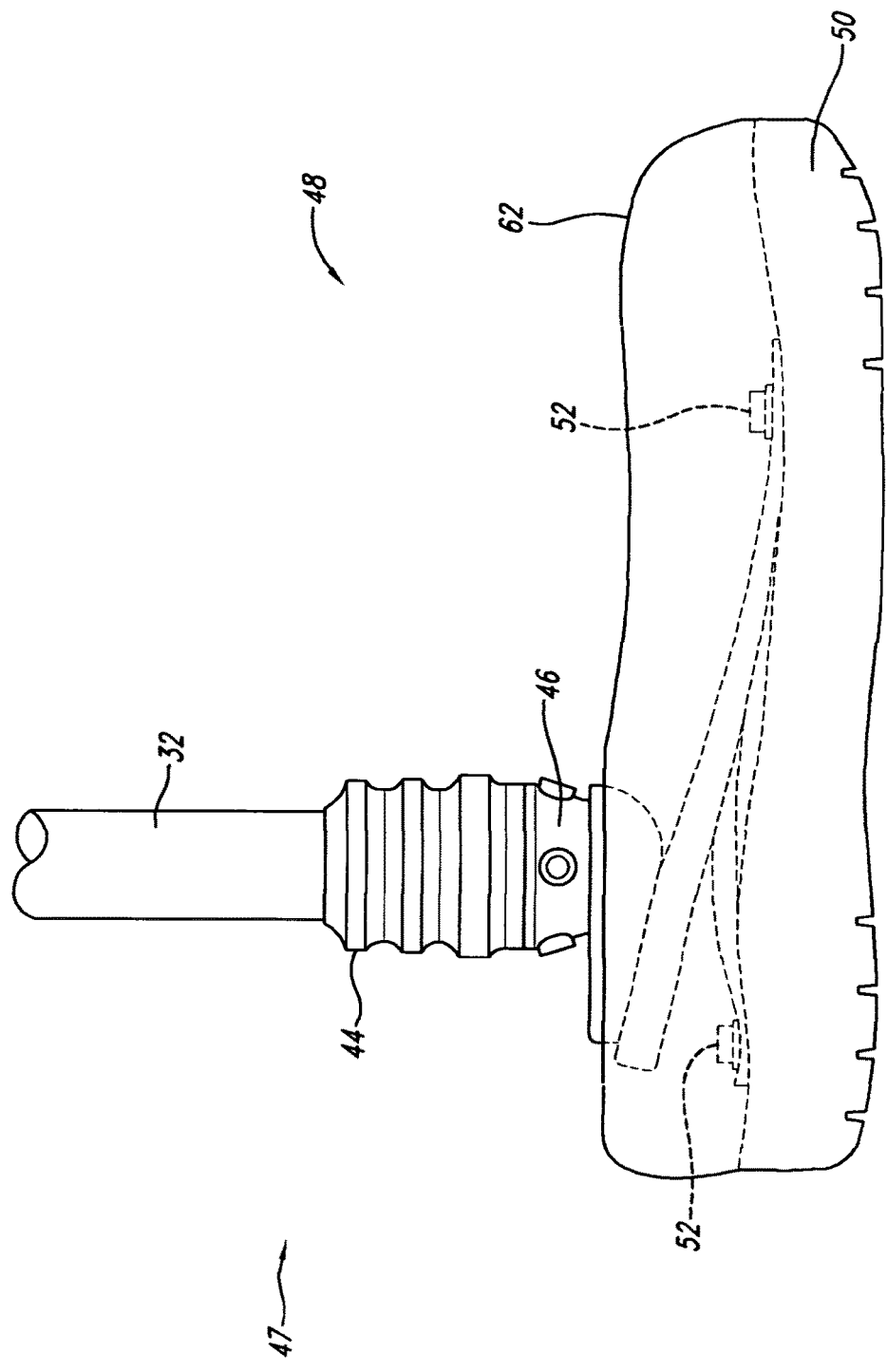
FIG. 30 is a right elevational view of an alternative implementation of the foot portion having a full upper shoe, for use in snowboard bindings, bicycle toe cages, snowshoes, crampons, water ski bindings, and/or other slip-in type bindings.

The foot 48 may be comprised of a shoe 50 and/or any number of shoe fastener(s) 52. Additionally, the shoe 50 may be removed from the foot 48 via the fastener(s) 52, providing the ability to change the shoe in order to suit any number of various activities. The shoe 50 can vary in form and function, examples include: a standard shoe sole such as shown in FIG. 25, a snowboarding or wakeboarding clip-in shoe with lateral clip bars 54 such as shown in FIG. 26, a cross country ski shoe with a toe clip 56 such as shown in FIG. 27, a downhill snow ski shoe with a toe clip 56 and heel clip 58 such as shown in FIG. 28, a bicycling shoe with a clipless system 60 such as shown in FIG. 29, and/or a shoe having a full upper portion 62 for use in various strap-in bindings such, as shown in FIG. 30.

Additional Embodiments

FIG. 24 illustrates, for example, adjustable fluidic shock absorber 38*d* embodied as an adjustable pneumatic shock absorber.

Elastic middle portion 17 of elastic member(s) 18 represented herein is composed of a resilient material having a decided level of elasticity for storing and releasing energy. As discussed herein, the user chooses elastic member 18 based on it's level of elasticity, the activity for which it will be used in, and according to his or her body weight, wherein a stiffer level of elasticity stores and releases more energy than a softer level of elasticity. The overall length and level of elasticity of the elastic member 18 determines the preloaded tension on the system.

Upper retaining ball 22 and lower retaining ball 24 on opposing longitudinal ends of elastic member 18 are optionally composed of a stiffer or more rigid material than elastic middle portion 17, which hinders deformation of retaining balls 22 and 24 for promoting retention in ball retainers 25, while elastic middle portion 17 is composed of a different softer or less rigid material which provides elastic deformation for promoting storing and releasing of energy. End upper and lower retaining balls 22 and 24 composed of the stiffer or more rigid material are substantially continuous with elastic middle portion 17 composed of different softer or less rigid material. For example, different more and less rigid materials are injected into different portions of the die during injection molding of elastic member 18.

Alternatively, retaining balls 22 and 24 and elastic middle portion 17 of elastic member 18 are optionally composed of the same material but having different hardness or durometer, wherein retaining balls 22 and 24 are relatively harder with a higher durometer, while elastic middle portion 17 is relatively softer with a lower durometer. End upper and lower retaining balls 22 and 24 composed of the relatively harder with a higher durometer material are substantially continuous with elastic middle portion 17 composed of different relatively softer with a lower durometer material. For example, different compositions of the same material having different higher and lower durometers are injected into different portions of the die during injection molding of elastic member 18.

Additionally, upper ball retainers 26 located on upper portion 102, which accept upper retaining ball 22 on end of elastic member 18, such as shown by example and without limitation in FIG. 1, are optionally formed independently of upper portion 102. Upper ball retainers 26 are, for example, injection molded of an injection moldable material such as an epoxy graphite material that forms a substantially rigid structure for receiving upper retaining ball 22. Independent molded upper ball retainers 26 are glued, adhesively adhered, mechanically fastened, or otherwise rigidly bonded in an appropriate position on upper portion 102. Accordingly, upper ball retainers 26 are easily moveable to different positions on upper portion 102 to suit the current needs of the user.

Retaining balls 22 and 24 stay secured in ball retainers 25 through the existing preload tension of elastic member 18.

Figure 31B:
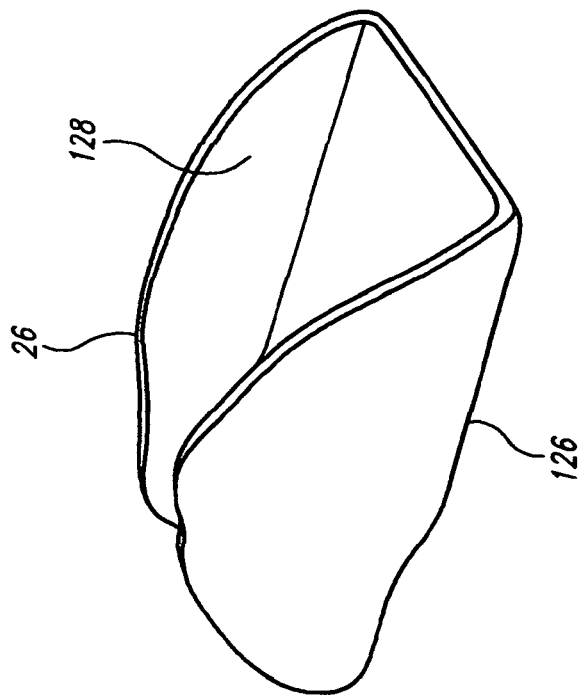
FIG. 31A and FIG. 31B are different views that illustrate one embodiment of upper ball retainers which are formed independently of an upper portion of the prosthesis system and coupled thereto in a desired position.
Figure 31A:
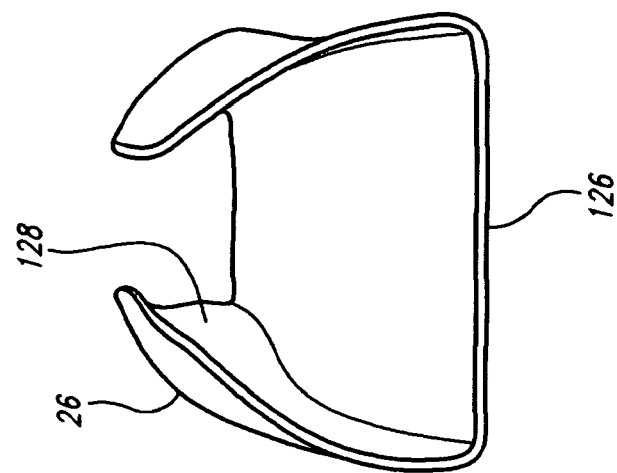

FIG. 31A and FIG. 31B are different views that illustrate one embodiment of upper ball retainers 26 which are formed independently of upper portion 102 and coupled thereto in a desired position. Therefore, upper ball retainers 26 is a socket that is removable and replaceable on upper portion 102. Upper ball retainers 26 located on upper portion 102 have mounting surfaces 126 shaped to conform to the surface of upper portion 102. Accordingly, upper ball retainer sockets 26 can be coupled by adhesive bonding to the surface of upper portion 102, else upper ball retainer sockets 26 can be coupled to the surface of upper portion 102 by fasteners.

Figure 2:
FIG. 2 is a side elevational view of an elastic member.
Figure 3:
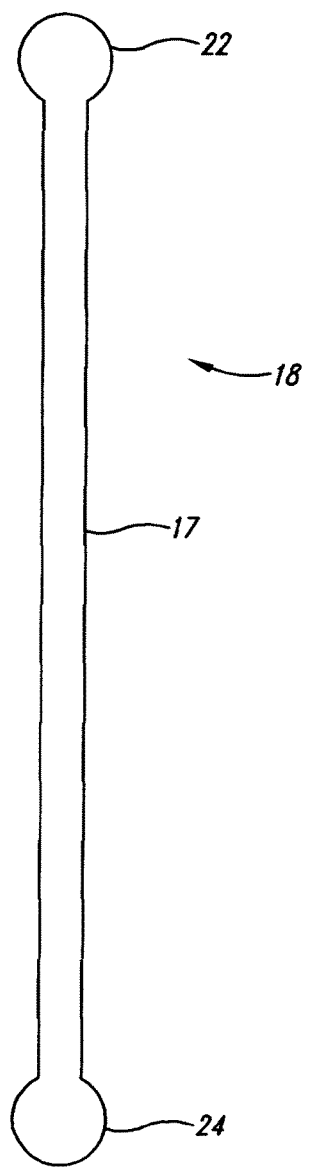
FIG. 3 is a front elevational view of the elastic member depicted in FIG. 2.
Figure 4:
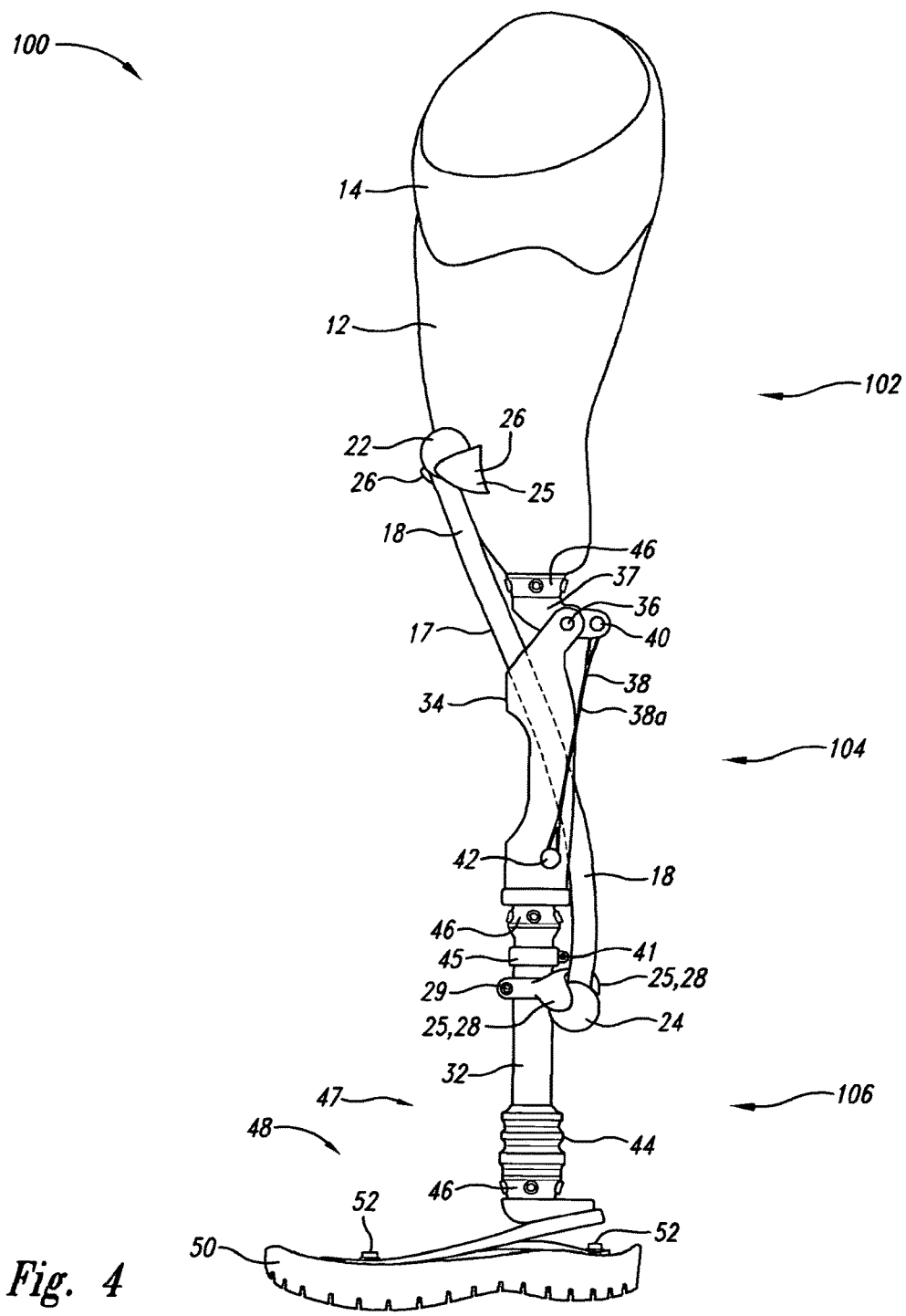
FIG. 4 is a left elevational view of an implementation of the prosthesis system depicted in FIG. 1.
Figure 5:
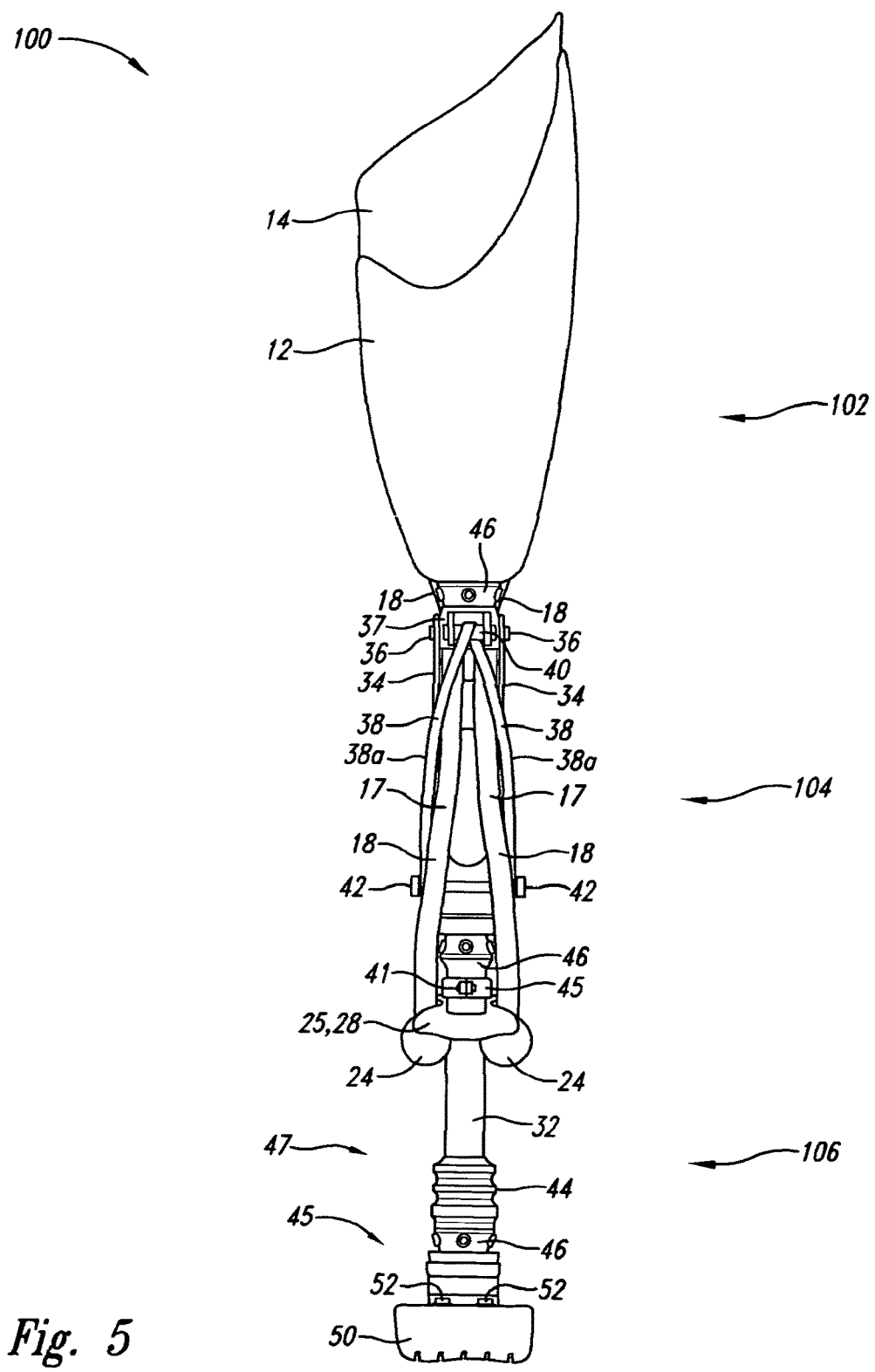
FIG. 5 is a rear elevational view of an implementation of the prosthesis system depicted in FIG. 1.

Upper ball retainer sockets 26 are formed with receiver sockets 128 shaped to accept upper retaining ball 22 on end of elastic member 18. For example, as illustrated in FIG. 2 and FIG. 3, upper retaining ball 22 and lower retaining ball 24 on opposing longitudinal ends of elastic member 18 are substantially spherical in shape, and upper ball retainers 26 are substantially hemispherical in shape for receiving thereinto substantially spherical upper retaining ball 22, as illustrated in FIG. 1.

Alternatively, receiver sockets 128 of upper ball retainers 26 are part-hemispherical shaped for receiving an alternative part-spherical upper retaining ball 122 on end of elastic member 18, as disclosed herein.

Figure 32:
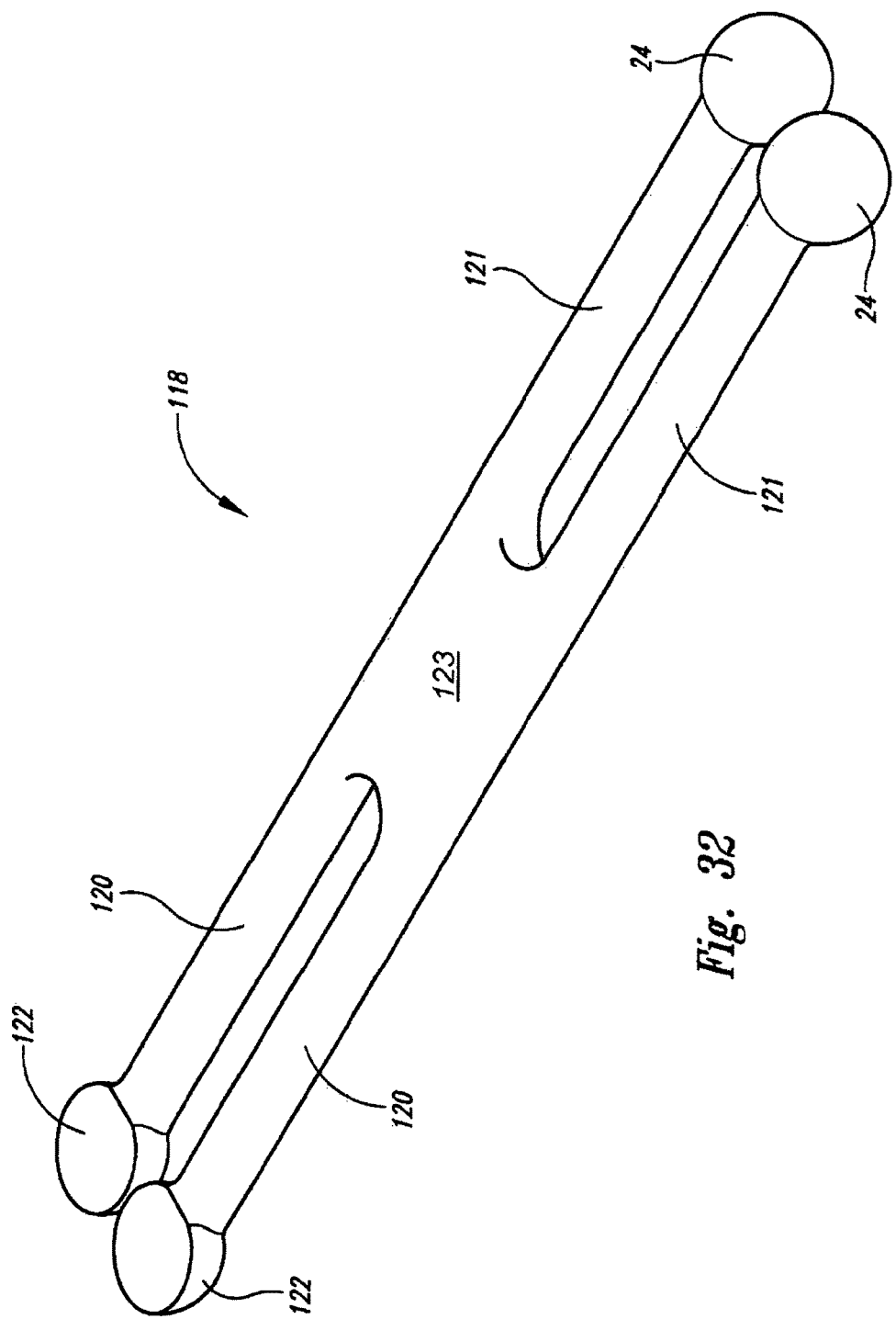
FIG. 32 illustrates an alternative part-spherical upper retaining ball on an alternative progressive elastic member or tendon having a plurality of upper and lower elastic cord portions extended in a spider Y-shape, X-shape or H-shape from a common hub portion.

FIG. 32 illustrates alternative part-spherical upper retaining ball 122 on an alternative progressive elastic member or tendon 118 having a plurality of upper and lower elastic cord portions 120 and 121 extended in a spider Y-shape, X-shape or H-shape from a hub portion 123. Here, alternative elastic member 118 is illustrated by example and without limitation as having a plurality of upper elastic cord portions 120 and a plurality of lower elastic cord portions 121 extended in a spider H-shape from hub portion 123. However, spider shape of alternative elastic member 118 is optionally any of a X-shape or H-shape or Y-shape with more or fewer of either upper or lower elastic cord portions 120 and 121, without deviating from the scope and intent of the present invention. Upper elastic cord portions 120 of alternative elastic member 118 are illustrated as being formed with alternative part-spherical upper retaining ball 122, which cooperate with part-hemispherical upper ball retainers or upper ball retainer sockets 26 for providing a low profile alternative to substantially spherical upper retaining ball 22 for substantially undetectable use under conventional clothing.

Lower elastic cord portions 121 alternative elastic member 118 are illustrated as having substantially spherical lower retaining ball 24. However, an alternative part-spherical lower retaining ball similar to alternative part-spherical upper retaining ball 122 is optionally substituted therefor without deviating from the scope and intent of the present invention.

As discussed herein regarding elastic members 18, upper and lower retaining balls 122 and 24 are optionally composed of a stiffer or more rigid material than upper and lower elastic cord portions 120, 121, which hinders deformation of retaining balls 122 and 24 for promoting retention in ball retainers 25, while elastic cord portions 120, 121 are composed of a different softer or less rigid material which provides greater elastic deformation for promoting alternately storing and releasing of energy.

Alternatively, also as discussed herein regarding elastic members 18, retaining balls 122 and 24 of elastic member 18 are optionally composed of the same material as upper and lower elastic cord portions 120, 121 but having different hardness or durometer, wherein retaining balls 122 and 24 are relatively harder with a higher durometer, while elastic cord portions 120, 121 are relatively softer with a lower durometer. Similarly to the stiffer or more rigid material composition, the higher durometer hinders deformation of retaining balls 122 and 24 for promoting retention in ball retainers 25, while similarly to the softer or less rigid material composition, the lower durometer provides greater elastic deformation for promoting alternately storing and releasing of energy.

Here, hub portion 123 is formed with an increased cross-section relative to elastic cord portions 120, 121. This increased cross-section results in hub portion 123 being stiffer than elastic cord portions 120, 121 such that hub portion 123 has a higher spring rate than elastic cord portions 120, 121, which hinders deformation of hub portion 123 and results in a different higher spring rate relative to softer elastic cord portions 120, 121.

Optionally, as discussed herein regarding progressive elastic members 18, increased cross-section hub portion 123 is optionally composed of a relatively stiffer or more rigid material than upper and lower elastic cord portions 120, 121. Alternatively, also as discussed herein regarding elastic members 18, hub portion 123 is optionally composed of the same material as upper and lower elastic cord portions 120, 121 but having different hardness or durometer, wherein hub portion 123 is relatively harder with a relatively higher durometer, while elastic cord portions 120, 121 are relatively softer with a relatively lower durometer. When composed of either relatively more rigid or relatively higher durometer material hub portion 123 is of relatively higher spring rate than lower spring rate, stretchier upper and lower elastic cord portions 120, 121 which are composed of relatively less rigid or relatively lower durometer material. Accordingly, alternative elastic member or tendon 118 provides progressive increase in resistance to bending knee joint 37, wherein stretchier upper and lower elastic cord portions 120, 121 are initially active for providing a slower or gentler increase in bending resistance, until stiffer hub portion 123 latterly becomes active for providing a faster or stiffer increase in bending resistance. Latter introduction of the faster or stiffer increase in bending resistance provided by stiffer hub portion 123 effectively gently slows and finally substantially stops bending before hyper-rotation of knee joint 37 where hard stops are encountered.

During bending of knee joint 37, alternative progressive elastic member or tendon 118 stores energy progressively in both stiffer hub portion 123 and stretchier upper and lower elastic cord portions 120, 121. In extension, alternative progressive elastic member or tendon 118 releases energy progressively from both stiffer hub portion 123 and stretchier upper and lower elastic cord portions 120, 121.

Alternative progressive elastic member or tendon 118 thus provides an initial high rate of energy release followed by progressive decrease in energy release during unbending and extension of knee joint 37, wherein relatively stiffer hub portion 123 is initially active for providing a relatively faster release of energy, until relatively stretchier upper and lower elastic cord portions 120, 121 latterly become active for providing a relatively slower or gentler energy release. Initial introduction of the relatively faster release of energy provided by stiffer hub portion 123 thus effectively provides an initial jolt of power on straightening, while latter introduction of the relatively slower or gentler release of energy provided by relatively stretchier upper and lower elastic cord portions 120, 121 effectively gently slows and finally substantially stops unbending before hyperextension of knee joint 37 where hard anti-hyperextension member 38 are encountered.

Hub portion 123 is optionally positioned substantially at the middle of alternative elastic member 118 such that lower elastic cord portions 121 are of substantially identical length as upper elastic cord portions 120. Alternatively, hub portion 123 is offset alternative elastic member 118 such that upper and lower elastic cord portions 120, 121 are of different lengths, whereby hub portion 123 is positionable substantially directly over knee fulcrum 36.

Routing of alternative elastic member(s) 118 can take the form of various configurations described herein.

Figure 33:
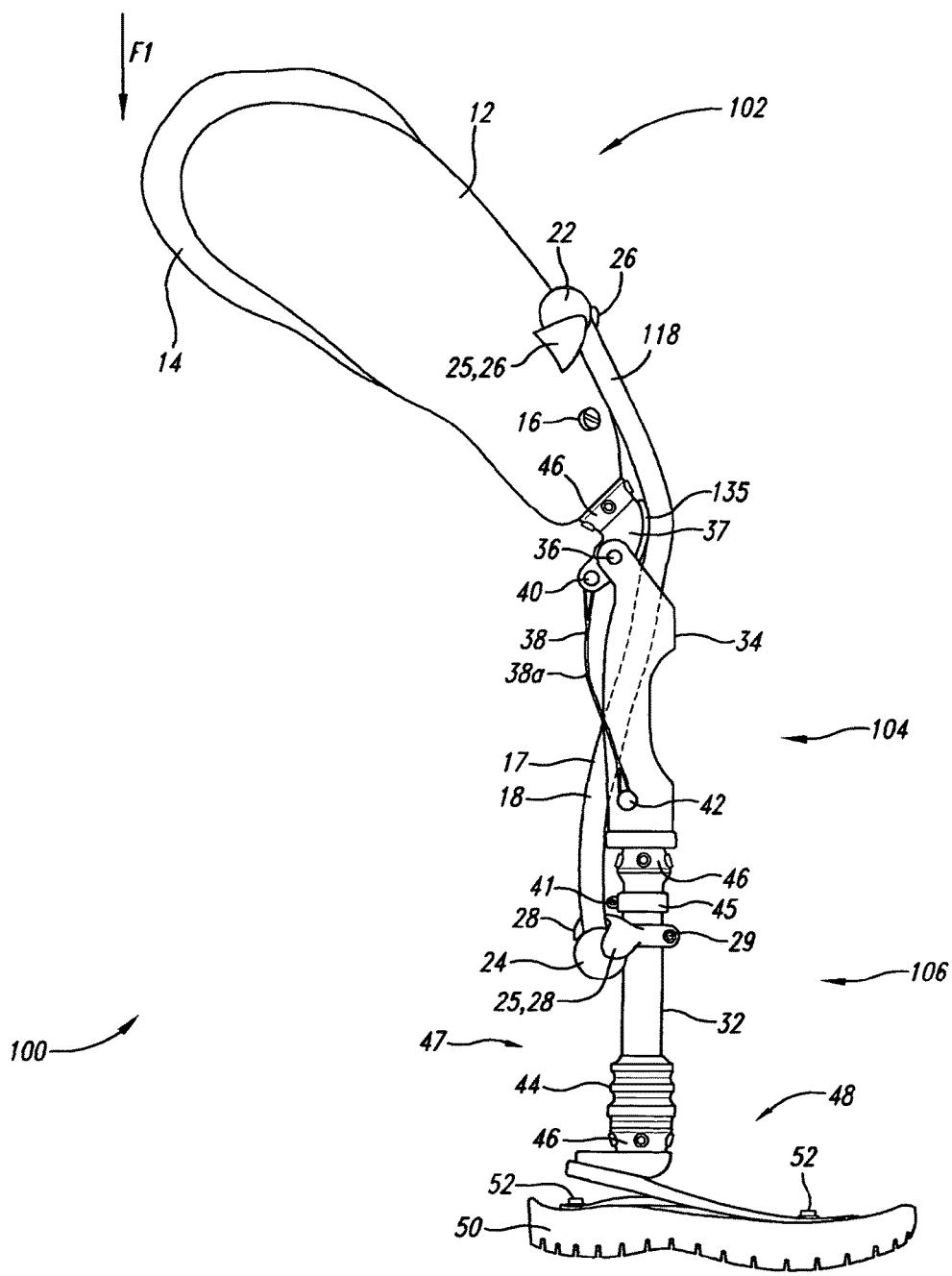
FIG. 33 illustrates one embodiment wherein an artificial patella is provided adjacent to a knee joint of the prosthesis system and anterior thereof for protecting the hub portion of the alternative elastic member illustrated in FIG. 32.

FIG. 33 illustrates one embodiment wherein an artificial patella 135 is provided adjacent to knee joint 37 and anterior thereof for protecting hub portion 123 of alternative elastic member 118. For example, artificial patella 135 is formed of a non-stick and wear-resistant material such as nylon, Teflon® or Delrin® that permits hub portion 123 to slide over knee joint 37 during bending and extension of upper and lower portions 102 and 106 about joint portion 104. Artificial patella 135 also permits fabrics to slide over knee joint 37 during bending and extension for protecting user's clothing when elastic members 18 are substituted for alternative elastic member 118 having hub portion 123.

Figure 34:
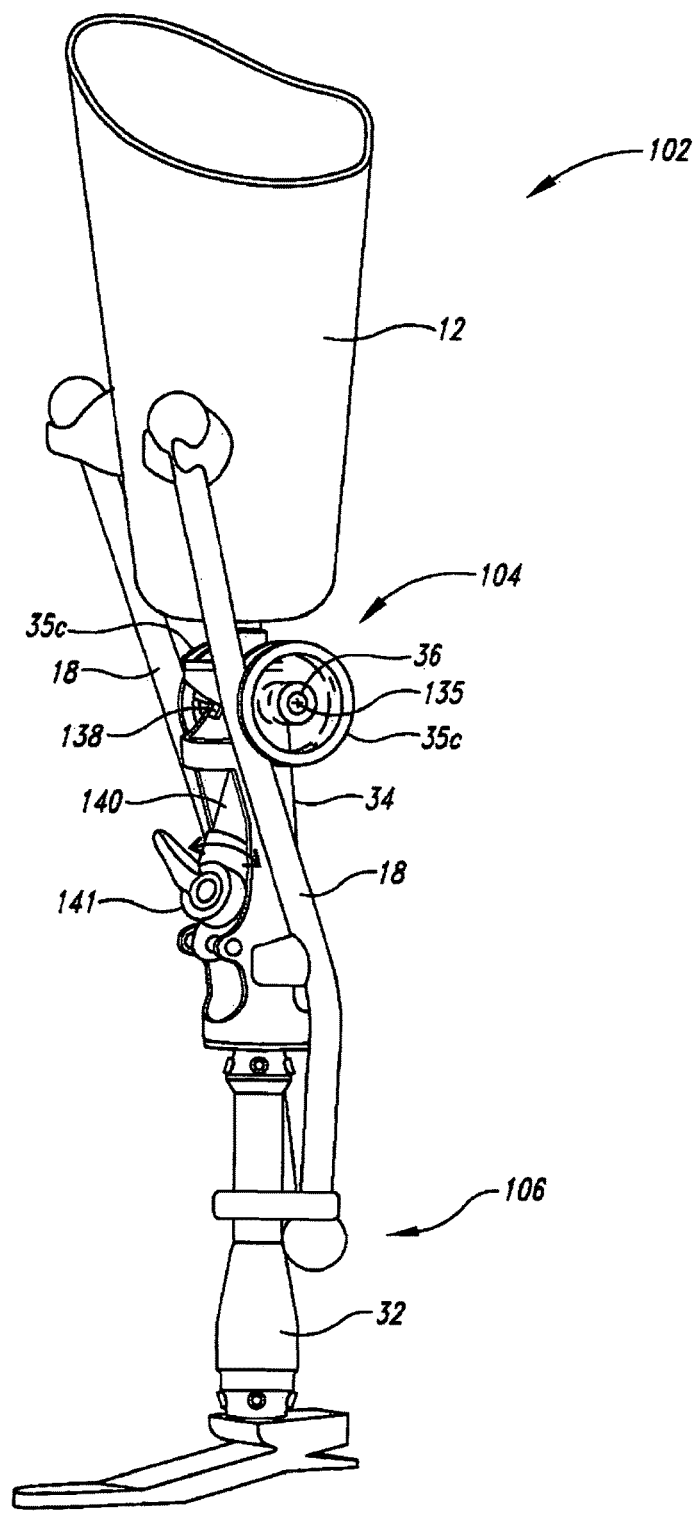
FIG. 34 is a pictorial anterior view of one alternative embodiment of the prosthesis system alternately shown with an adjustable pneumatic shock absorber.

FIG. 34 is a pictorial anterior view of one alternative embodiment of prosthesis system 100 alternately shown with an adjustable pneumatic shock absorber 140. Hydraulic shock absorbers have been known in prior art prosthesis systems. However, such hydraulic shock absorbers fail to provide either a smooth stroke or a progressive compression and/or rebound. Pneumatic operation of alternative adjustable pneumatic shock absorber 140 provides both a relatively smoother stroke as compared with the typical sticky and uneven stroke of known prior art hydraulic shock absorbers, and also provides a relatively progressive compression and/or rebound as compared with the typical constant compression and abrupt stop of known prior art hydraulic shock absorbers.

Furthermore, hydraulic shock absorbers of known prior art prosthesis systems fail to provide ease of response adjustment. Response of such hydraulic shock absorbers is typically adjustable only by changing the fluid pressure in the hydraulic cylinder, else changing out a hydraulic cylinder of one pressure for a hydraulic cylinder of a different pressure. As compared with the limited ability of hydraulic shock absorbers for adjusting response, alternative adjustable pneumatic shock absorber 140 provides easy response adjustment by simple opening and closing (arrow) of an air restriction valve 141 between internal chambers, wherein restricting the air flow between internal chambers stiffens response, while opening air flow between internal chambers softens response.

Alternative adjustable pneumatic shock absorber 140 is similarly useful with either one or more elastic member(s) 18 or alternative progressive elastic member or tendon 118.

FIG. 34 also illustrates joint portion 104 including a pair of alternative rotational retaining elements 35*c* each configured as a substantially round wheel or pulley that is rotatable about an axis 137 substantially parallel to or aligned with knee fulcrum 36. Alternative rotational retaining elements 35*c* secure retention of middle portion 17 and guide elastic member 18 during bending and extension of upper and lower portions 102 and 106 about joint portion 104. Alternative rotational retaining elements 35*c* are similarly useful for securing retention of either upper elastic cord portions 120 or lower elastic cord portions 121 and guiding alternative spider-shaped progressive elastic member or tendon 118 during bending and extension of upper and lower portions 102 and 106 about joint portion 104.

Figure 35:
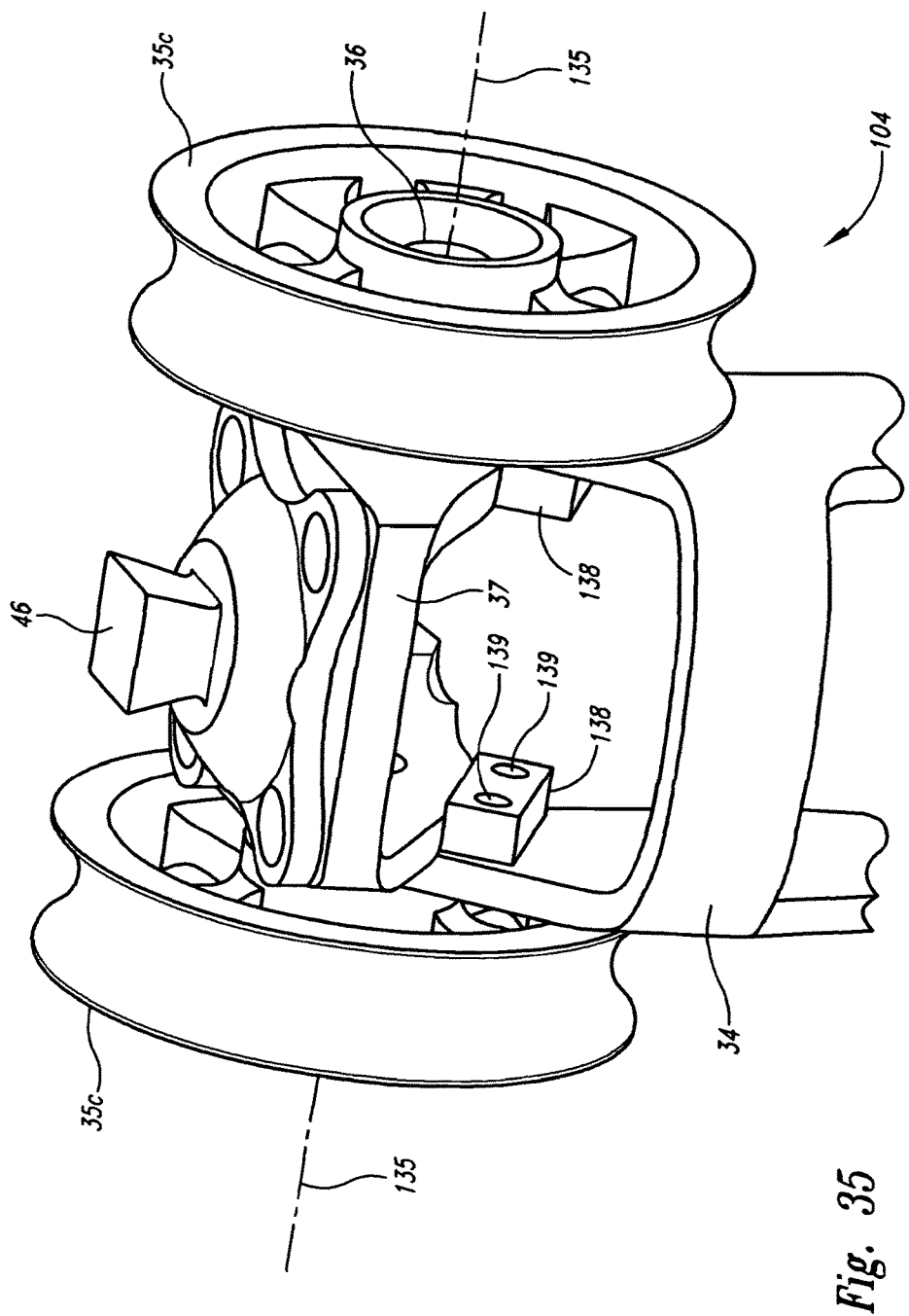
FIG. 35 illustrates one adjustable anti-hyperextension member that is optionally integrated into the prosthesis system for preventing hyperextensions of the joint portion of the prosthesis system.

FIG. 35 illustrates one adjustable anti-hyperextension member 138 that is optionally integrated into prosthesis system 100 for prevent hyperextensions of joint portion 104. Here, adjustable anti-hyperextension member 138 is illustrated by example and without limitation as one or more rigid stops mounted on knee frame 34 in a position within joint portion 104 for interfering with hyperextensions of knee joint 37. For example, a pair of anti-hyperextension stops 138 are removably mounted by one or more fasteners 139 on knee frame 34 adjacent to knee fulcrum 36 in positions for being encountered by knee joint 37 at the end of its extension. Anti-hyperextension member 138 is adjustable by removing and replacing the rigid stops mounted on knee frame 34 by fasteners 139. Anti-hyperextension member(s) 138 is adjustable for varying a pre-bend of joint portion 104 for different activities, for example, for normal walking, or for extreme sports. For example, anti-hyperextension stops 138 are changed between different sizes of rigid stops for pre-bending of joint portion 104 in a substantially upright orientation at about four and one-half (4-½) degrees for normal walking, or about eight and one-half (8-½) degrees to ten (10) degrees for extreme sports. Other structures for anti-hyperextension member(s) 138 and means for mounting may take the form of various configurations and are also contemplated and may be substituted without deviating from the scope and intent of the present invention.

Anti-hyperextension stops 138 are optionally made of a non-marring slightly resilient sacrificial material, such as nylon, Teflon® or Delrin® that permits some shock absorption, or a non-resilient material, such as anodized or coated aluminum that provided long and durable life without significant shock absorption.

Prosthesis system 100 is represented herein by example and without limitation as a prosthetic leg. However, prosthesis system 100 is optionally an arm having upper portion 102 being an upper arm in a position proximate to the user's body, lower portion 106 being a forearm in a position distal from the user's body, and joint portion 104 being an elbow joint. When prosthesis system 100 is optionally an arm, ankle segment 47 is a wrist segment, and appendage 48 is a hand or other useful appurtenance or accessory.

Alternative Embodiment

Figure 36:
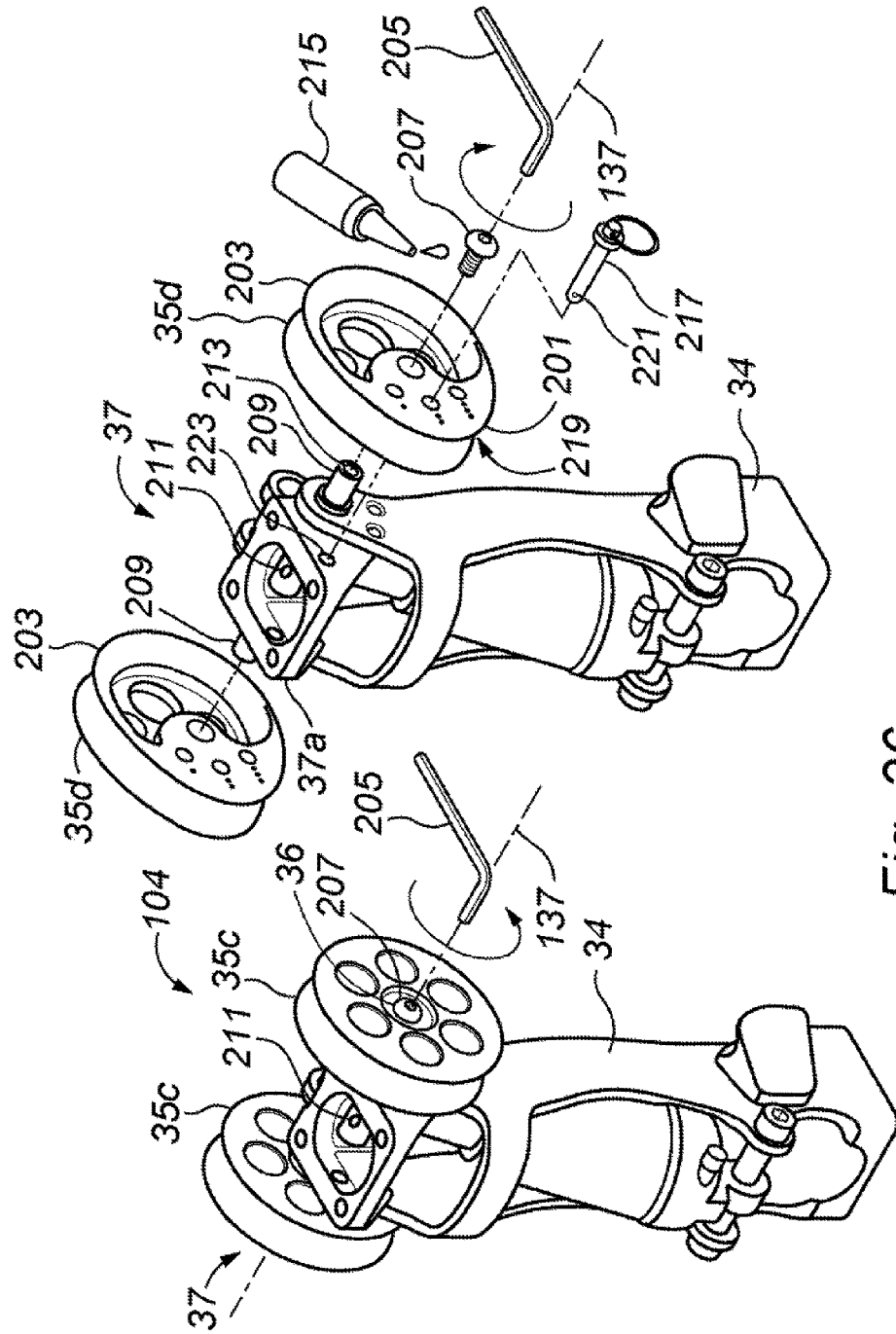
FIG. 36 is a pictorial anterior view of one alternative embodiment of prosthesis system of the invention alternately shown with the alternative rotational retaining elements of FIG. 34 and FIG. 35 being replaced with alternative rotational cam having an adjustable range of knee flexion effect.

FIG. 36 is a pictorial anterior view of one alternative embodiment of prosthesis system 100 alternately shown with alternative rotational retaining elements 35c being replaced with alternative rotational cam 35d having an adjustable range of knee flexion effect.

The cam shape wheel of alternative cam rotational retaining elements 35d provides different amounts of flexion tension during bending and extension of upper and lower portions 102 and 106 about knee joint 37 of joint portion 104. This variation in flexion tension is provided by varying the length of elastic members 18 during bending of joint portion 104 by changing the displacement of the middle portion 17 of the elastic member 18 about knee fulcrum 36, which coincides with the knee rotational axis 137. For example, different portions of the lobe 201 of the cam shape wheel forming alternative cam rotational retaining elements 35d extend different distances from the base circle portion 203 thereof. Because the middle portion 17 of the elastic member 18 is seated on lobe 201 of alternative cam rotational retaining elements 35d, the middle portion 17 of the elastic member 18 is displaced closer or further from the knee fulcrum 36 depending upon the portion of the lobe 201 that is presented in front of knee fulcrum 36. The amount of increased stretch of the middle portion 17 of the elastic member 18 during bending of joint portion 104 depends upon the portion of the lobe 201 that is presented in front of knee fulcrum 36. During rotation of the knee joint 37 of joint portion 104 about knee rotational axis 137, the displacement of lobe 201 forces the middle portion 17 of the elastic member 18 to stretch further than the base circle portion 203 of alternative cam rotational retaining elements 35d. This variable amount of stretch of elastic member middle portion 17 provides a variation within a range of knee flexion effect provided by alternative cam rotational retaining elements 35d that results in elastic member 18 exhibiting different amount of flexion tension during bending. Thus, the range of knee flexion effect provided by alternative cam rotational retaining elements 35d results in elastic member 18 exhibiting different amount of flexion tension during bending and extension of upper and lower portions 102 and 106 about knee joint 37 of joint portion 104.

Alternative cam rotational retaining elements 35d is optionally configured as a simple cam-shaped seat. FIG. 36 illustrates joint portion 104 including a pair of alternative cam rotational retaining elements 35d each configured as a cam or cam-shaped pulley for a more secure retention of the middle portion 17. Alternative cam rotational retaining elements 35d is rotatable about an axis 137 substantially parallel to or aligned with knee fulcrum 36. Alternative cam rotational retaining elements 35d secure retention of middle portion 17 and guide elastic member 18 during bending and extension of upper and lower portions 102 and 106 about knee joint 37 of joint portion 104, as disclosed herein relative to alternative rotational retaining elements 35c. For example, cam shape wheel of alternative cam rotational retaining elements 35d is formed as a pulley sized to receive thereinto a lengthwise portion of middle portion 17 of elastic members 18 for secure retention of the middle portion 17 relative to joint portion 104.

Alternative cam rotational retaining elements 35d are similarly useful for securing retention of either upper elastic cord portions 120 or lower elastic cord portions 121 and guiding alternative spider-shaped progressive elastic member or tendon 118 during bending and extension of upper and lower portions 102 and 106 about knee joint 37, as disclosed herein relative to alternative rotational retaining elements 35c. Alternatively, alternative cam rotational retaining elements 35d are adaptable for securing retention of hub portion 123 and guiding alternative spider-shaped progressive elastic member or tendon 118 during bending and extension of upper and lower portions 102 and 106 about knee joint 37, as disclosed herein.

Alternative cam rotational retaining elements 35d are a retrofit of alternative prosthesis system 100 having alternative rotational retaining elements 35c. FIG. 36 illustrates (right) removal of alternative rotational retaining elements 35c, and installation (left) of alternative cam rotational retaining elements 35d. Here, elastic members 18 are first removed from alternative rotational retaining elements 35c to relieve tension off of knee unit 34. Method of removing elastic members 18 is disclosed herein. Next, both left and right alternative rotational retaining elements 35c are removed. For example, using a wrench 205 button head retaining screw 207 is unscrewed from the end of the pivot shaft 209. A center hole 211 is provided in the pivot shaft 209 in which a lever (not shown) is lodged to prevent pivot shaft 209 from turning, which aids in unscrewing retaining screw 207 from end of pivot shaft 209.

As shown in FIG. 36 (left), with alternative rotational retaining elements 35c removed, the end of the main pivot shaft 209 is optionally cleaned and a small amount of lubricant, such as a lithium-based grease, is applied thereto. This lubricant aids in ensuring a clean and lubricated bearing surface for the alternative cam rotational retaining elements 35d. Operator is expected to take care not to apply lubricant to the internal threads 213 of the main pivot shaft 209 because the button head retaining screw 207 fastens into these threads 213.

Before installing the alternative cam rotational retaining elements 35d, means are provided for ensuring retaining screw 207 remains secure. For example, a lock washer or a medium strength chemical thread locker 215, such as blue Loctite 242, is applied to the button head retaining screw 207 which may be the same or a new replacement screw. Alternative cam rotational retaining elements 35d are installed onto the pivot shaft 209 on either side of knee joint 37. A wrench 205 is utilized for tightening the button head retaining screw 207 on pivot shaft 209, again while using a lever lodged in the center hole 211 of the pivot shaft 209 to prevent shaft 209 from turning.

Means are provided for selecting different adjusted rotations of alternative cam rotational retaining elements 35d relative to joint portion 104 for resulting in different greater or lesser range of knee flexion effect, which in turn results in elastic member 18 exhibiting different amount of flexion tension during bending and extension of upper and lower portions 102 and 106 about joint portion 104. For example, here user inserts a locking pin 217 into one of the plurality of rotation adjustment position holes 219 (three shown) through alternative cam rotational retaining elements 35d such that, as locking pin 217 lines up with a correlating flexion tension adjustment hole 223 in an upper portion 37a of knee joint 37, pushing pin 217 in until detent or ball lock 221 on pin 217 engages to lock pin 217 into place.

Optionally, the user inserts locking pin 217 into the rotation adjustment position hole 219 of only one of the two alternative cam rotational retaining elements 35d such that only one of the two elastic members 18 is affected. Or, the user inserts one of the locking pin 217 into the rotation adjustment position hole 219 of both of the two alternative cam rotational retaining elements 35d such that both of the two elastic members 18 is affected.

User may, optionally, inserts locking pin 217 into different ones of the three rotation adjustment position holes 219 of each of the two alternative cam rotational retaining elements 35d such that each of the two elastic members 18 is affected differently from the other. User thus has a wide range of variations of which one, or both, and to what degree the one, or both, of the two elastic members 18 is affected by the two alternative cam rotational retaining elements 35d. Accordingly, the user can "fine tune" the effect of using the two alternative cam rotational retaining elements 35d, whereby user can adjust the response of the limb prosthesis on the fly to accommodate any activity.

As discussed herein, by allowing the user to apply the force F1 of his or her own body weight, the system seeks a bent position. In other words, the upper portion 102 rotates around the knee fulcrum 36 and down towards the lower portion 106, as shown if FIGS. 7 and 8. This may in some respects mimic the bending of a knee. While in a bent position the elastic member(s) 18 are further stressed and applying a tensional force between the upper portion 102 and lower portion 106, such as shown in FIGS. 7 and 8. The tensional force applied by the elastic member(s) 18 will return the system to a resting position when the force F1 of the user's body weight is diminished or removed, such as shown in FIG. 6. In some respects this may mimic the function of the quadriceps muscles of the leg, acting as an extensor. The alternative cam rotational retaining elements 35d permit wearer to vary the tensional force applied by the elastic member(s) 18 between the upper portion 102 and lower portion 106 by varying the displacement of the middle portion 17 of the elastic member 18 about knee fulcrum 36.

Figure 37:
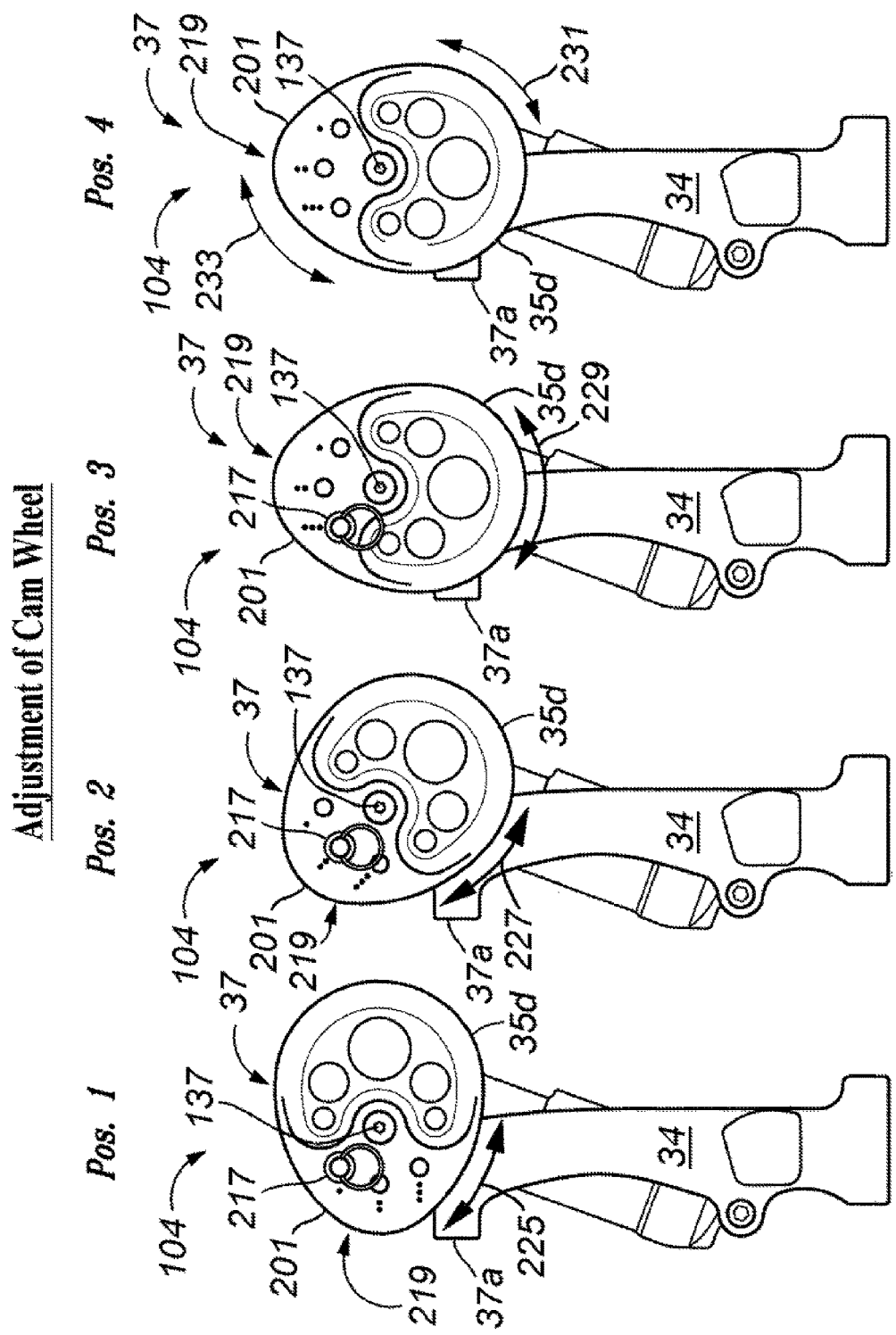
FIG. 37 illustrates adjustment of the alternative rotational retaining elements of FIG. 36 for different amount of tendon flexion tension during bending and extension of the joint.

FIG. 37 illustrates adjustment of alternative cam rotational retaining elements 35d.

During rotation of the knee joint 37 of joint portion 104 about knee rotational axis 137, the displacement of lobe 201 forces the middle portion 17 of the elastic member 18 to stretch further than the base circle portion 203 of alternative cam rotational retaining elements 35d. In the views shown for Positions 1-4, alternative cam rotational retaining elements 35d rotates with bending of knee joint 37 such that the middle portion 17 of the elastic member 18 encounters a different surface portion of alternative cam rotational retaining elements 35d that results in greater or lesser displacement from the rotational axis 137 of knee joint 37 of joint portion 104.

Position 1 (left) is shown with locking pin 217 inserted a into a first one of the plurality of rotation adjustment position holes 219 (designated with a single dot) through alternative cam rotational retaining elements 35d such that locking pin 217 lines up with a correlating flexion tension adjustment hole 223 in upper portion 37a of knee joint 37, and locks rotational retaining elements 35d into place relative to upper portion 37a of knee joint 37. Thus, during rotation of the knee joint 37 of joint portion 104 about knee rotational axis 137, the minimum displacement of lobe 201 forces the middle portion 17 of the elastic member 18 to stretch only a small distance further than the base circle portion 203 of alternative cam rotational retaining elements 35d. Accordingly, Position 1 presents a surface portion 225 of lobe 201 of alternative cam rotational retaining elements 35d that results in a minimum amount of cam effect with flexion of joint portion 104.

Position 2 (center left) is shown with locking pin 217 inserted a into a second one of the plurality of rotation adjustment position holes 219 (designated with two dots) through alternative cam rotational retaining elements 35d such that locking pin 217 lines up with a correlating flexion tension adjustment hole 223 in upper portion 37a of knee joint 37, and locks rotational retaining elements 35d into place relative to upper portion 37a of knee joint 37. Thus, during rotation of the knee joint 37 of joint portion 104 about knee rotational axis 137, the medium displacement of lobe 201 forces the middle portion 17 of the elastic member 18 to stretch a larger distance further than the base circle portion 203 of alternative cam rotational retaining elements 35d. Accordingly, Position 2 presents a surface portion 227 of lobe 201 of alternative cam rotational retaining elements 35d that results in a mid-range amount of cam effect with flexion of joint portion 104.

Position 3 (center right) is shown with locking pin 217 inserted a into a third one of the plurality of rotation adjustment position holes 219 (designated with three dots) through alternative cam rotational retaining elements 35d such that locking pin 217 lines up with a correlating flexion tension adjustment hole 223 in upper portion 37a of knee joint 37, and locks rotational retaining elements 35d into place relative to upper portion 37a of knee joint 37. Thus, during rotation of the knee joint 37 of joint portion 104 about knee rotational axis 137, the maximum displacement of lobe 201 forces the middle portion 17 of the elastic member 18 to stretch the largest distance further than the base circle portion 203 of alternative cam rotational retaining elements 35d. Accordingly, Position 3 presents a surface portion 229 of lobe 201 of alternative cam rotational retaining elements 35d that results in a maximum amount of cam effect with flexion of joint portion 104.

Position 4 (right) is shown with locking pin 217 removed such that alternative cam rotational retaining elements 35d is permitted to float (arrow 231) and settle into a neutral position relative to knee joint 37 during rotation thereof. Position 4 presents a surface portion of alternative cam rotational retaining elements 35d that results in the very least amount of flexion tension in the elastic member(s) 18 during bending of joint portion 104. Thus, during rotation of the knee joint 37 of joint portion 104 about knee rotational axis 137, alternative cam rotational retaining elements 35d is permitted to rotate with the elastic middle portion 17 of elastic member 18, whereby elastic middle portion 17 encounters a minimum displacement of alternative cam rotational retaining elements 35d. Thus, the middle portion 17 of the elastic member 18 stretches the least distance of alternative cam rotational retaining elements 35d. Accordingly, Position 4 presents a surface portion 233 of the base circle portion 203 of alternative cam rotational retaining elements 35d that results in a minimum amount of cam effect with flexion of joint portion 104.

Position 4 is suggested if the very least amount of flexion tension with the elastic member(s) 18 is desired because the cam shape of alternative cam rotational retaining elements 35d will not engage at all during bending of joint portion 104.

Additionally, positional variations of alternative cam rotational retaining elements 35d are optionally combined with adjustments to adjustable fluidic shock absorber 38d, such as shown in FIG. 24, or adjustments to adjustable pneumatic shock absorber 140, such as shown in FIG. 34, which may be adjustable by simple opening and closing (arrow) of the air restriction valve 141. Thus, positional variations of alternative cam rotational retaining elements 35d are multiplied by adjustments to fluidic shock absorber 38d or pneumatic shock absorber 140 to result in an even wider range of variation in flexion tension produced by elastic member 18 during rotation of joint portion 104.

Figure 38:
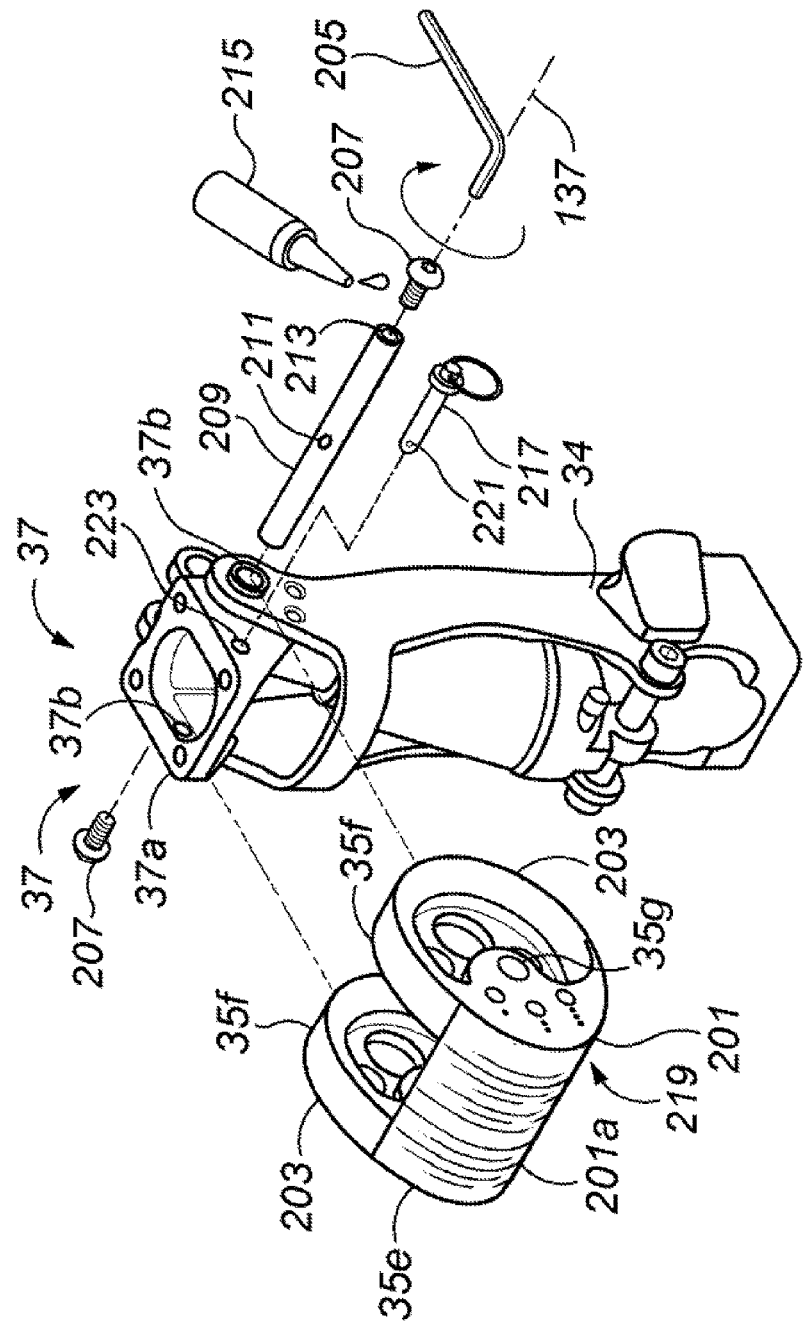
FIG. 38 illustrates another alternative cam rotational retaining element being adapted for securing retention of a hub portion of the alternative spider-shaped progressive elastic member or tendon shown in FIG. 32, during bending and extension of the joint.

FIG. 38 illustrates another alternative cam rotational retaining element 35e being adapted for securing retention of hub portion 123 and guiding alternative spider-shaped progressive elastic member or tendon 118, shown in FIG. 32, during bending and extension of upper and lower portions 102 and 106 about knee joint 37. Here, alternative cam rotational retaining element 35e is formed with a lobe 201a that extends between two cam wheel portions 35f that fit onto opposite ends of the pivot shaft 209, which provides a central support for securing retention of hub portion 123.

For example, the two cam wheel portions 35f of alternative cam rotational retaining element 35e are fitted over knee joint 37, and mounting holes 35g in the two cam wheel portions 35f are aligned with knee rotational axis 137 and bearings 37b of knee joint 37. The pivot shaft 209 is fit through aligned mounting holes 35g and bearings 37b. The knee joint 37 is secured using retaining screws 207, as disclosed herein. Thereafter, the locking pin 217 is inserted into one of the plurality of rotation adjustment position holes 219 (three shown) through one or both of alternative cam rotational retaining elements 35e such that, as locking pin 217 lines up with a correlating flexion tension adjustment hole 223 in an upper portion 37a of knee joint 37, pin 217 is pushed in until detent or ball lock 221 on pin 217 engages to lock pin 217 into place.

Hub portion 123 of alternative spider-shaped progressive elastic member or tendon 118 is then seated over lobe 201a of alternative cam rotational retaining element 35e, whereby alternative cam rotational retaining element 35e operates similarly to alternative cam rotational retaining elements 35d, as disclosed herein, for resulting in a different greater or lesser range of knee flexion effect relative to joint portion 104.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A prosthesis system for a human limb, the prosthesis system comprising:
   a proximate portion configured for coupling with the human limb;
   a distal portion configured for coupling with a prosthetic appendage;
   a joint portion, the proximate portion hingedly coupled to the distal portion via the joint portion such that the distal portion and the proximate portion are pivotally movable with respect to one another between an extended state and a bent state; and
   an elongated elastic cord member comprising an elastic portion between first and second end portions and substantially continuous therewith and are further more rigid than the elastic portion therebetween, the first end portion coupled to a first retainer positioned on the proximate portion, and the second end portion coupled to a second retainer positioned on the distal portion; and
   a mid-portion retaining element positioned between the first and second retainers for supporting a portion of the elastic portion of the elongated elastic cord member between the first and second end portions thereof, wherein the mid-portion retaining element comprises a means for varying the amount of flexion tension exhibited by the elastic cord member during rotation of the distal portion relative to the proximate portion within a range of flexion tension.

2. The system of claim 1, wherein at least one of the first and second end portions of the elastic cord member further comprises a part-spherical retaining ball, and at least one retaining element further comprises a ball retainer that is shaped to slidably accept the corresponding part-spherical retaining ball end portion of the elastic cord member.

3. The system of claim 2, wherein at least the first end portion of the elongated elastic cord member further comprises a part-hemispherical shape, and at least the first retainer positioned on further comprises a part-hemispherical shape for slidably receiving thereinto the first part-hemispherical end portion.

4. The system of claim 1, wherein the mid-portion retaining element is further positioned adjacent to the joint portion for supporting a portion of the elastic portion of the elastic cord member adjacent to the joint portion.

5. The system of claim 1, wherein the means for varying the amount of flexion tension exhibited by the elastic cord member during rotation of the distal portion relative to the proximate portion within a range of flexion tension further comprises a means for varying a displacement of the portion the previously presented elastic portion of the elongated elastic cord relative to the joint portion.

6. The system of claim 5, wherein the means for varying a displacement of the portion of the elastic portion of the elongated elastic cord relative to the joint portion further comprises a means for fixedly adjusting a displacement thereof from the joint portion.

7. The system of claim 6, wherein the mid-portion retaining element further comprises a cam-shaped retaining element.

8. The system of claim 7, further comprising a means for fixing the cam-shaped retaining element with a displacement of different portions of a retaining surface thereof from the joint portion at a plurality of different displacements therefrom within a range of displacements.

9. The system of claim 1, further comprising a prosthetic appendage coupled to the distal portion of the prosthetic system.

10. A prosthesis system for attaching to a distal portion of a residual human limb, the prosthesis system comprising:
    an upper portion of the prosthetic system configured for coupling with a residual limb remaining after amputation, the upper portion further comprising one or more first retaining elements;
    a lower portion of the prosthetic system comprising a coupler that is structured for coupling with a prosthetic appendage and further comprising one or more second retaining elements;
    a joint portion of the prosthetic system hingedly coupling the upper portion of the prosthetic system to the lower portion of the prosthetic system such that the lower portion and the upper portion are respectively pivotally movable between an extended state and a bent state; and one or more elongated elastic members of the prosthetic system, each of the cord members comprising an elongated elastic portion between first and second end portions of material that is stiffer than the elastic portion therebetween and substantially continuous therewith, the first end portion coupled to one of the one or more first retaining elements of the upper portion of the prosthetic system and the second end portion coupled to one of the one or more second retaining elements of the lower portion of the prosthetic system, each of the elongated elastic members having a first length between the first portion and the second portion in the extended state and a second length between the first portion and the second portion in the bent state, the first length being shorter than the second length; and a third retaining element of the prosthetic system, the third retaining element coupled to one of the upper portion or the lower portion between the one or more first retaining elements and the one or more second retaining elements, the third retaining element being positioned for supporting the relatively elastic portion of one or more of one or more the elongated elastic members between the first and second end portions thereof, wherein the third retaining element of the prosthetic system further comprises a plurality of retaining surface portions displaceable different displacement distances from the fulcrum.

11. The system of claim 10, wherein the third retaining element of the prosthetic system is further positioned proximate to the joint portion of the prosthetic system.

12. The system of claim 11, wherein the joint portion of the prosthetic system further comprises a fulcrum, and the third retaining element of the prosthetic system is further coupled to the fulcrum.

13. The system of claim 12, wherein the third retaining element of the prosthetic system is further rotatable about the fulcrum.

14. The system of claim 10, wherein the third retaining element of the prosthetic system further comprises a cam-shaped retaining element comprising the plurality of retaining surface portions along a cam surface thereof, and locking elements coupled for fixing the cam-shaped element retaining with different retaining surface portions positioned for supporting the relatively elastic portion at different displacements from the fulcrum.

15. The system of claim 10, further comprising a prosthetic appendage coupled to the lower portion of the prosthetic system.

16. A prosthesis system for a human limb, the prosthesis system comprising:

an upper proximate portion configured for coupling with the limb and further comprising a first retainer positioned thereon;

a lower distal portion comprising a second retainer positioned thereon, and further comprising a structure for coupling with an artificial appendage;

a joint portion, the upper proximate portion hingedly coupled to the lower distal portion via the joint portion such that the lower distal portion and the upper proximate portion are pivotally movable with respect to one another between an extended state and a bent state; and an elongated elastic member comprising a resiliently stretchable material between first and second end portions thereof, wherein the first end portion is coupled to the first retainer of the upper proximate portion and the second end portion is coupled to the second retainer of the lower distal portion, the elongated member having a first length between the first end portion and the second end portion in the extended state and a second length between the first end portion and the second end portion in the bent state, the second length being longer than the first length due to a stretching of at least a mid-portion of the resilient material between the first end portion and the second end portion of the elongated member when the upper proximate portion and the lower distal portion are pivotally moved between the extended state and the bent state; and a mid-portion elastic member retainer positioned between the first and second retainers for supporting a portion of the resiliently stretchable material of the elastic member between the first and second end portions thereof, and displacing the portion of the resiliently stretchable material a distance from the joint portion, wherein the mid-portion elastic member retainer is further adjustable for displacing the portion of the resiliently stretchable material at a plurality of different displacement distances from the joint portion.

17. The system of claim 16, wherein the mid-portion elastic member retainer further comprises a plurality of different retaining surface portions adapted for receiving the portion of the resiliently stretchable material, the different retaining surface portions being further displaceable at different displacement distances from the joint portion.

18. The system of claim 17, wherein the mid-portion elastic member retainer is further fixable relative to the joint portion fixedly positioning the different retaining surface portions at the different displacement distances therefrom.

19. The system of claim 16, further comprising a prosthetic appendage coupled to the lower distal portion of the prosthetic system.

* * * * *